United States Patent
Chen et al.

(10) Patent No.: US 9,962,534 B2
(45) Date of Patent: May 8, 2018

(54) MICROARRAY FOR DELIVERY OF THERAPEUTIC AGENT, METHODS OF USE, AND METHODS OF MAKING

(71) Applicant: Corium International, Inc., Menlo Park, CA (US)

(72) Inventors: Guohua Chen, Sunnyvale, CA (US); Zhongli Ding, Sunnyvale, CA (US); Esi Ghartey-Tagoe, San Jose, CA (US); Ashutosh Shastry, Santa Clara, CA (US); Robert Wade Worsham, Cupertino, CA (US); Parminder Singh, Union City, CA (US)

(73) Assignee: Corium International, Inc., Menlo Park, CA (US)

( * ) Notice: Subject to any disclaimer, the term of this patent is extended or adjusted under 35 U.S.C. 154(b) by 379 days.

(21) Appl. No.: 14/214,377

(22) Filed: Mar. 14, 2014

(65) Prior Publication Data
US 2014/0272101 A1   Sep. 18, 2014

Related U.S. Application Data

(60) Provisional application No. 61/792,069, filed on Mar. 15, 2013.

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0053* (2013.01)

(58) Field of Classification Search
CPC ........... H05B 33/08; B29C 43/02; A61M 5/00

USPC .......... 604/506; 264/319; 313/503
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |

(Continued)

FOREIGN PATENT DOCUMENTS

| | | |
|---|---|---|
| CA | 2376285 | 12/2000 |
| CA | 2316534 | 3/2001 |

(Continued)

OTHER PUBLICATIONS

Chun, et al., "An array of hollow microcapillaries for the controlled injection of genetic materials into animal/plant cells," IEEE Workshop on Micro Electro Mechanical Systems, pp. 406-411, (1999).

(Continued)

*Primary Examiner* — Dah-Wei D Yuan
*Assistant Examiner* — Andrew Bowman
(74) *Attorney, Agent, or Firm* — Judy Mohr; Claine Snow; McDermott Will & Emery LLP

(57) ABSTRACT

Devices and methods for using and manufacturing microstructure arrays are described.

25 Claims, 9 Drawing Sheets

(56) References Cited

U.S. PATENT DOCUMENTS

| | | | |
|---|---|---|---|
| 4,117,841 | A | 10/1978 | Perrotta et al. |
| 4,151,240 | A | 4/1979 | Lucas et al. |
| 4,180,232 | A | 12/1979 | Hardigg |
| 4,342,314 | A | 8/1982 | Radel et al. |
| 4,381,963 | A | 5/1983 | Goldstein et al. |
| 4,395,215 | A | 7/1983 | Bishop |
| 4,402,696 | A | 9/1983 | Gulko |
| 4,460,368 | A | 7/1984 | Allison et al. |
| 4,460,370 | A | 7/1984 | Allison et al. |
| 4,463,045 | A | 7/1984 | Ahr et al. |
| 4,509,908 | A | 4/1985 | Mullane, Jr. |
| 4,515,168 | A | 5/1985 | Chester et al. |
| 4,556,441 | A | 12/1985 | Faasse, Jr. |
| 4,585,991 | A | 4/1986 | Reid et al. |
| 4,597,961 | A | 7/1986 | Etscorn |
| 4,609,518 | A | 9/1986 | Curro et al. |
| 4,630,603 | A | 12/1986 | Greenway |
| 4,743,249 | A | 5/1988 | Loveland |
| 4,784,737 | A | 11/1988 | Ray et al. |
| 4,812,305 | A | 3/1989 | Vocal |
| 4,837,049 | A | 6/1989 | Byers et al. |
| 4,846,821 | A | 7/1989 | Lyons et al. |
| 4,904,475 | A | 2/1990 | Gale et al. |
| 4,996,159 | A | 2/1991 | Glaser |
| 5,051,259 | A | 9/1991 | Olsen et al. |
| 5,061,258 | A | 10/1991 | Martz |
| 5,134,079 | A | 7/1992 | Cusack et al. |
| 5,139,029 | A | 8/1992 | Fishman et al. |
| 5,156,591 | A | 10/1992 | Gross et al. |
| 5,158,073 | A | 10/1992 | Bukowski |
| 5,160,315 | A | 11/1992 | Heinecke et al. |
| 5,162,043 | A | 11/1992 | Lew et al. |
| 5,190,558 | A | 3/1993 | Matsushita et al. |
| 5,198,192 | A | 3/1993 | Saito et al. |
| 5,215,088 | A | 6/1993 | Normann et al. |
| 5,244,677 | A | 9/1993 | Kreckel et al. |
| 5,244,711 | A | 9/1993 | Drelich et al. |
| 5,250,023 | A | 10/1993 | Lee et al. |
| 5,250,067 | A | 10/1993 | Gelfer et al. |
| 5,252,279 | A | 10/1993 | Gore et al. |
| 5,256,360 | A | 10/1993 | Li |
| 5,279,544 | A | 1/1994 | Gross et al. |
| 5,308,625 | A | 5/1994 | Wong et al. |
| 5,318,557 | A | 6/1994 | Gross |
| 5,320,600 | A | 6/1994 | Lambert |
| 5,330,452 | A | 7/1994 | Zook |
| 5,362,307 | A | 11/1994 | Guy et al. |
| 5,383,512 | A | 1/1995 | Jarvis |
| 5,457,041 | A | 10/1995 | Ginaven et al. |
| 5,462,743 | A | 10/1995 | Turner et al. |
| 5,476,443 | A | 12/1995 | Cartmell et al. |
| 5,487,726 | A | 1/1996 | Rabineau et al. |
| 5,496,304 | A | 3/1996 | Chasan |
| 5,498,235 | A | 3/1996 | Flower |
| 5,503,843 | A | 4/1996 | Santus et al. |
| 5,512,219 | A | 4/1996 | Rowland et al. |
| 5,520,629 | A | 5/1996 | Heinecke et al. |
| 5,527,288 | A | 6/1996 | Gross et al. |
| 5,531,675 | A | 7/1996 | Yoo |
| 5,531,855 | A | 7/1996 | Heinecke et al. |
| 5,536,263 | A | 7/1996 | Rolf et al. |
| 5,551,953 | A | 9/1996 | Lattin et al. |
| 5,567,376 | A | 10/1996 | Turi et al. |
| 5,591,123 | A | 1/1997 | Sibalis et al. |
| 5,591,139 | A | 1/1997 | Lin et al. |
| 5,611,806 | A | 3/1997 | Jang |
| 5,645,977 | A | 7/1997 | Wu et al. |
| 5,658,515 | A | 8/1997 | Lee et al. |
| 5,662,127 | A | 9/1997 | De Vaughn |
| 5,676,850 | A | 10/1997 | Reed et al. |
| 5,681,580 | A | 10/1997 | Jang et al. |
| 5,697,901 | A | 12/1997 | Eriksson |
| 5,704,520 | A | 1/1998 | Gross |
| 5,711,761 | A | 1/1998 | Untereker et al. |
| 5,728,089 | A | 3/1998 | Lal et al. |
| 5,730,714 | A | 3/1998 | Guy et al. |
| 5,730,721 | A | 3/1998 | Hyatt et al. |
| 5,735,273 | A | 4/1998 | Kurnik et al. |
| 5,738,642 | A | 4/1998 | Heinecke et al. |
| 5,756,117 | A | 5/1998 | D'Angelo et al. |
| 5,771,890 | A | 6/1998 | Tamada |
| 5,788,983 | A | 8/1998 | Chien et al. |
| 5,800,420 | A | 9/1998 | Gross et al. |
| 5,807,375 | A | 9/1998 | Gross et al. |
| 5,814,020 | A | 9/1998 | Gross |
| 5,820,622 | A | 10/1998 | Gross et al. |
| 5,827,183 | A | 10/1998 | Kurnik et al. |
| 5,843,114 | A | 12/1998 | Jang |
| 5,848,985 | A | 12/1998 | Muroki |
| 5,848,990 | A | 12/1998 | Cirelli et al. |
| 5,848,991 | A | 12/1998 | Gross et al. |
| 5,851,549 | A | 12/1998 | Svec |
| 5,855,801 | A | 1/1999 | Lin et al. |
| 5,873,849 | A | 2/1999 | Bernard |
| 5,879,326 | A | 3/1999 | Godshall et al. |
| 5,900,252 | A | 5/1999 | Calanchi et al. |
| 5,932,240 | A | 8/1999 | D'Angelo et al. |
| 5,938,684 | A | 8/1999 | Lynch et al. |
| 5,948,488 | A | 9/1999 | Marecki et al. |
| 5,962,011 | A | 10/1999 | Devillez et al. |
| 5,964,729 | A | 10/1999 | Choi et al. |
| 5,983,136 | A | 11/1999 | Kamen |
| 5,987,989 | A | 11/1999 | Yamamoto et al. |
| 5,997,549 | A | 12/1999 | Sauceda et al. |
| 5,997,986 | A | 12/1999 | Turi et al. |
| 6,014,584 | A | 1/2000 | Hofmann et al. |
| 6,023,629 | A | 2/2000 | Tamada |
| 6,024,553 | A | 2/2000 | Shimalia |
| 6,036,659 | A | 3/2000 | Ray et al. |
| 6,038,465 | A | 3/2000 | Melton, Jr. |
| 6,038,485 | A | 3/2000 | Axelgaard |
| 6,047,208 | A | 4/2000 | Flower |
| 6,050,988 | A | 4/2000 | Zuck |
| 6,055,453 | A | 4/2000 | Hofmann et al. |
| 6,083,196 | A | 7/2000 | Trautman et al. |
| 6,091,975 | A | 7/2000 | Daddona et al. |
| 6,106,751 | A | 8/2000 | Talbot et al. |
| 6,120,792 | A | 9/2000 | Juni |
| 6,129,696 | A | 10/2000 | Sibalis |
| 6,132,449 | A | 10/2000 | Lum et al. |
| 6,132,755 | A | 10/2000 | Eicher et al. |
| 6,135,990 | A | 10/2000 | Heller et al. |
| 6,136,008 | A | 10/2000 | Becker et al. |
| 6,156,336 | A | 12/2000 | Bracht |
| 6,169,224 | B1 | 1/2001 | Heinecke et al. |
| 6,181,964 | B1 | 1/2001 | Hofmann et al. |
| 6,183,434 | B1 | 2/2001 | Eppstein |
| 6,183,770 | B1 | 2/2001 | Muchin et al. |
| 6,187,210 | B1 | 2/2001 | Lebouitz et al. |
| 6,216,034 | B1 | 4/2001 | Hofmann et al. |
| 6,219,574 | B1 | 4/2001 | Cormier et al. |
| 6,230,051 | B1 | 5/2001 | Cormier et al. |
| 6,241,701 | B1 | 6/2001 | Hofmann |
| 6,248,120 | B1 | 6/2001 | Wyszogrodzki |
| 6,256,533 | B1 | 7/2001 | Yuzhakov et al. |
| 6,293,925 | B1 | 9/2001 | Safabash et al. |
| 6,312,612 | B1 | 11/2001 | Sherman et al. |
| 6,322,808 | B1 | 11/2001 | Trautman et al. |
| 6,334,856 | B1 | 1/2002 | Allen et al. |
| 6,355,054 | B1 | 3/2002 | Neuberger |
| 6,375,627 | B1 | 4/2002 | Mauze et al. |
| 6,375,870 | B1 | 4/2002 | Visovsky et al. |
| 6,375,978 | B1 | 4/2002 | Kleiner et al. |
| 6,379,324 | B1 | 4/2002 | Garstein et al. |
| 6,440,096 | B1 | 8/2002 | Lastovich et al. |
| 6,451,240 | B1 | 9/2002 | Sherman et al. |
| 6,471,903 | B2 | 10/2002 | Sherman et al. |
| 6,476,288 | B1 | 11/2002 | Van Rijswijck et al. |
| 6,494,830 | B1 | 12/2002 | Wessel |
| 6,503,231 | B1 | 1/2003 | Prausnitz et al. |
| 6,508,947 | B2 | 1/2003 | Gulvin et al. |
| 6,511,463 | B1 | 1/2003 | Wood et al. |
| 6,516,223 | B2 | 2/2003 | Hofmann |
| 6,532,386 | B2 | 3/2003 | Sun et al. |

(56) References Cited

U.S. PATENT DOCUMENTS

| | | |
|---|---|---|
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,476 B2 | 11/2003 | Gartstein et al. |
| 6,652,478 B1 | 11/2003 | Gartstein et al. |
| 6,656,147 B1 | 12/2003 | Gerstek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,763,203 B2 | 7/2010 | Arias et al. |
| 7,785,301 B2 | 8/2010 | Yuzhakov |
| 7,798,987 B2 | 9/2010 | Trautman et al. |
| 7,828,827 B2 | 11/2010 | Gartstein et al. |
| 7,914,480 B2 | 3/2011 | Cleary et al. |
| 8,057,842 B2 | 11/2011 | Choi et al. |
| 8,216,190 B2 | 7/2012 | Gartstein et al. |
| 8,366,677 B2 | 2/2013 | Kaspar et al. |
| 8,702,726 B2 | 4/2014 | Gartstein et al. |
| 8,821,446 B2 | 9/2014 | Trautman et al. |
| 8,911,749 B2 | 12/2014 | Ghartey-Tagoe et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193819 A1 | 12/2002 | Porter et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0261631 A1 | 11/2005 | Clarke et al. |
| 2006/0024358 A1 | 2/2006 | Santini et al. |
| 2006/0076718 A1 | 4/2006 | Sherman et al. |
| 2006/0095061 A1 | 5/2006 | Trautman et al. |
| 2006/0108914 A1* | 5/2006 | Young ........................ 313/503 |
| 2006/0129174 A1 | 6/2006 | Gartstein et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0195035 A1 | 8/2008 | Frederickson et al. |
| 2008/0208146 A1 | 8/2008 | Brandwein et al. |
| 2008/0214987 A1 | 9/2008 | Xu |
| 2008/0269685 A1 | 10/2008 | Singh et al. |
| 2009/0017210 A1 | 1/2009 | Andrianov et al. |
| 2009/0043279 A1 | 2/2009 | Kaspar et al. |
| 2009/0155330 A1 | 6/2009 | Ghartey-Tagoe et al. |
| 2009/0216215 A1 | 8/2009 | Thaimann et al. |
| 2010/0028390 A1 | 2/2010 | Cleary et al. |

(56) References Cited

U.S. PATENT DOCUMENTS

| | | | |
|---|---|---|---|
| 2010/0228203 A1 | 9/2010 | Quan et al. | |
| 2010/0247698 A1 | 9/2010 | Zhang et al. | |
| 2011/0006458 A1* | 1/2011 | Sagi et al. | 264/319 |
| 2011/0046638 A1 | 2/2011 | Gartstein et al. | |
| 2011/0121486 A1 | 5/2011 | Oh et al. | |
| 2011/0177139 A1 | 7/2011 | Hyungil et al. | |
| 2011/0276027 A1 | 11/2011 | Trautman et al. | |
| 2011/0276028 A1* | 11/2011 | Singh et al. | 604/506 |
| 2012/0150023 A1 | 6/2012 | Kaspar et al. | |
| 2012/0184906 A1 | 7/2012 | McAllister | |
| 2013/0131598 A1 | 5/2013 | Trautman et al. | |
| 2013/0292868 A1 | 11/2013 | Singh et al. | |
| 2013/0292886 A1 | 11/2013 | Sagi et al. | |
| 2014/0180201 A1 | 6/2014 | Ding et al. | |
| 2014/0272101 A1 | 9/2014 | Chen et al. | |
| 2014/0276366 A1 | 9/2014 | Bourne et al. | |
| 2014/0276378 A1 | 9/2014 | Chen et al. | |
| 2014/0276474 A1 | 9/2014 | Ding et al. | |
| 2014/0276580 A1 | 9/2014 | Le et al. | |
| 2014/0276589 A1 | 9/2014 | Bayramov et al. | |
| 2015/0079133 A1 | 3/2015 | Ghartey-Tagoe et al. | |

FOREIGN PATENT DOCUMENTS

| | | |
|---|---|---|
| CA | 2422907 | 4/2002 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-148485 A | 6/2001 |
| JP | 2001-157715 | 6/2001 |
| JP | 2001-341314 | 12/2001 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2007-190112 A | 1/2006 |
| JP | 2006-341089 A | 12/2006 |
| JP | 2007-130030 A | 5/2007 |
| JP | 2008-006178 A | 1/2008 |
| JP | 2008-194288 A | 8/2008 |
| JP | 2010-233674 A | 10/2010 |
| KR | 20100064669 A | 6/2010 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/006242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072169 | 9/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/024224 A1 | 3/2004 |
| WO | WO 2004/076339 | 9/2004 |
| WO | WO 2004/110717 | 12/2004 |
| WO | WO 2005/046769 A2 | 5/2005 |
| WO | WO 2005/082596 A1 | 9/2005 |
| WO | WO 2005/089857 A1 | 9/2005 |
| WO | WO 2005/094526 | 10/2005 |
| WO | WO 2006/020842 | 2/2006 |
| WO | WO 2006/055795 | 5/2006 |
| WO | WO 2006/086742 A2 | 8/2006 |
| WO | WO 2006/101459 A1 | 9/2006 |
| WO | WO 2007/002521 A2 | 1/2007 |

(56) References Cited

FOREIGN PATENT DOCUMENTS

| WO | WO 2007/002523 | | 1/2007 |
|---|---|---|---|
| WO | WO 2007/030477 | A2 | 3/2007 |
| WO | WO 2007/057806 | A2 | 7/2007 |
| WO | WO 2007/081430 | A2 | 7/2007 |
| WO | WO 2007/124411 | | 11/2007 |
| WO | WO 2008/011625 | | 1/2008 |
| WO | WO 2008/024141 | A2 | 2/2008 |
| WO | WO 2008/091602 | | 7/2008 |
| WO | WO 2008/130587 | | 10/2008 |
| WO | WO 2008/139648 | A1 | 11/2008 |
| WO | WO 2009/039013 | A1 | 3/2009 |
| WO | WO 2009/048607 | A1 | 4/2009 |
| WO | WO 2009/054988 | A1 | 4/2009 |
| WO | WO 2009/142741 | A1 | 11/2009 |
| WO | WO 2010/040271 | A1 | 4/2010 |
| WO | WO 2010/124255 | A2 | 10/2010 |
| WO | WO 2011/121023 | A1 | 10/2011 |
| WO | WO 2011/140240 | | 10/2011 |
| WO | WO 2011/140274 | | 10/2011 |
| WO | WO 2012/054582 | A2 | 4/2012 |
| WO | WO 2012/122163 | A1 | 9/2012 |
| WO | WO 2014/100750 | A1 | 6/2014 |
| WO | WO 2014/144973 | A1 | 9/2014 |
| WO | WO 2014/150069 | A1 | 9/2014 |
| WO | WO 2014/150285 | A2 | 9/2014 |
| WO | WO 2014/151654 | A1 | 9/2014 |
| WO | WO 2014/164314 | A1 | 10/2014 |

OTHER PUBLICATIONS

"extend", Merriam-Webster Online Dictionary, 6 pages, Downloaded on Sep. 7, 2010 from <http://www.merriam-webster.com/dictionary/extend>.

"extend", Macmillan Online Dictionary, 5 pages, Downloaded on Sep. 7, 2010 from <http://www.macmillandictionary.com/dictionary/american/extend>.

Henry, et al., "Micromachined microneedles for transdermal delivery of drugs", IEEE Workshop on Micro Electro Mechanical Systems, New York, NY, pp. 494-498, (1998).

Henry, et al., "Microfabricated microneedles: A novel approach to transdermal drug delivery", J. Pharmaceutical Science, vol. 87, No. 8, pp. 922-925, (1998).

"Heparin Pregnancy and Breast Feeding Warnings", Drugs.com, Accessed Oct. 8, 2009, <http://www.drugs.com/pregnancy/heparin.html>.

International Search Report from International Patent Application No. PCT/US2000/015612 dated Sep. 7, 2000.

International Search Report from International Patent Application No. PCT/US2000/015613 dated Sep. 6, 2000.

International Search Report from International Patent Application No. PCT/US2000/015614 dated Sep. 5, 2000.

International Search Report from International Patent Application No. PCT/US2001/031977 dated Apr. 29, 2002.

International Search Report from International Patent Application No. PCT/US2001/031978 dated Apr. 29, 2002.

International Search Report from International Patent Application No. PCT/US2002/014624 dated Sep. 3, 2002.

International Search Report from International Patent Application No. PCT/US2002/029228 dated Apr. 23, 2003.

International Search Report from International Patent Application No. PCT/US2002/029245 dated Dec. 27, 2002.

International Search Report from International Patent Application No. PCT/US2004/005382 dated Nov. 25, 2004.

International Search Report from International Patent Application No. PCT/US2004/017255 dated May 24, 2005.

International Search Report from International Patent Application No. PCT/US2005/009854 dated Jul. 3, 2008.

International Search Report from International Patent Application No. PCT/US2008/000824 dated Jul. 18, 2008.

International Search Report from International Patent Application No. PCT/US2008/004943 dated Jun. 9, 2009, application now published as International Publication No. WO2008/130587 Oct. 30, 2008

International Search Report from International Patent Application No. PCT/US2008/011635 dated Dec. 19, 2008, application now published as International Publication No. WO2009/048607 on Apr. 16, 2009.

International Search Report from International Patent Application No. PCT/US2010/032299 dated Dec. 10, 2010, application now published as International Publication No. WO2010/124255 on Oct. 28, 2010.

International Search Report from International Patent Application No. PCT/US2013/077281 dated Mar. 4, 2013.

International Search Report from International Patent Application No. PCT/US2014/022087 dated May 23, 2014.

International Search Report from International Patent Application No. PCT/US2014/022859 dated May 26, 2014.

International Search Report from International Patent Application No. PCT/US2014/029601 dated Jul. 1, 2014.

Matriano, et al., "Macroflux(R) microprojection array patch technology: A new and efficient approach for intracutaneous immunization", Pharm. Res., vol. 19, No. 1, pp. 63-70. (2002).

McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.

Mikszta, et al., "Improvred genetic immunization via micromechanical disruption of skin-barrier function and targeted epidermal delivery", Nat. Med., vol. 8, No. 4, pp. 415-419. (2002).

Mikszta, et al., "Protective immunization against inhalation anthrax: A comparison of minimally invasive delivery platforms", J. Inf. Dis., vol. 191, No. 2, pp. 278-288. (2005).

Papautsky, et al., "Micromachined Pipette Arrays," MPA, Proceedings—19th international Conference—IEEE/EMBS, Chicago IL, USA, pp. 2281-2284 (1997).

Park et al., "Biodegradable polymer microneedles: Fabrication, mechanics, and transdermal drug delivery", J. Contr. Rel., vol. 104, pp. 51-66 (2005).

Park, et al., "Polymer Microneedles for Controlled-Release Drug Delivery," Pharmaceutical Research, Kluwer Academic Publishers-Plenum Publishers, NE, vol. 23, No. 5, pp. 1008-1019 (2006).

Prausnitz, et al., "Transdermal transport efficiency during skin electroporation and iontophoresis", J. Contr. Release, vol. 38, pp. 205-217, (1996).

Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).

Rydberg, et al., "Low-molecular-weight heparin preventing and treating DVT", Am. Fam. Physician, vol. 59, No. 6, pp. 1607-1612, (1999).

Sivamani, et al., "Microneedles and transdermal applications", Exp. Opin. Drug Del., vol. 4, No. 1, pp. 19-25, (2007).

Wouters, et al., "Microelectrochemical systems for drug delivery", Electrochimica Acta., vol. 42, pp. 3385-3390, (1997).

Xia, et al., "Soft Lithography", Angew. Chem. Int. Ed., vol. 37, pp. 551-575, (1998).

Xia, et al., "Soft Lithography", Annu. Rev. Mater. Sci., vol. 28, pp. 153-184 (1998).

"Eudragit EPO Readymix—Taste masking and moisture protection have never been easier" Evonik Industries, Evonik Industries AG, Pharma Polymers & Services, Nov. 2014.

International Search Report from International Patent Application No. PCT/US2014/021841 dated Aug. 11, 2014.

International Search Report from International Patent Application No. PCT/US2014/022836 dated May 9, 2015.

International Search Report from International Patent Application No. PCT/US2014/026179 dated Jul. 18, 2014.

\* cited by examiner

FIG. 4A   FIG. 4B

MICROARRAY FOR DELIVERY OF THERAPEUTIC AGENT, METHODS OF USE, AND METHODS OF MAKING

CROSS-REFERENCE TO RELATED APPLICATIONS

This application claims the benefit of U.S. Provisional Application No. 61/792,069, filed Mar. 15, 2013, which is incorporated herein by reference in its entirety.

TECHNICAL FIELD

The disclosure relates generally to methods and delivery systems for transdermally administering a therapeutic agent, drug, or vaccine using an array of microstructures, methods for making or fabricating the systems, and related features thereof.

BACKGROUND

Arrays of microneedles were proposed as a way of administering drugs through the skin in the 1970s, for example in expired U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A further description of the fabrication of a microneedle array made of polyglycolic acid is found in Jung-Hwan Park et al., "Biodegradable polymer microneedles: Fabrication, mechanics, and transdermal drug delivery," J. of Controlled Release, 104:51-66 (2005).

A method of forming microprotrusion arrays using solvent casting methods is described in U.S. Publication No. 2008/0269685, which is incorporated in its entirety herein by reference.

A layered microstructure array has been described in U.S. Publication No. 2011/0276028, incorporated in its entirety herein, for hPTH delivery comprising a fast dissolving drug-in-tip distal layer and a backing layer formed of an insoluble biodegradable polymer.

Despite these efforts, there is still a need to find simpler and better methods for the manufacture of polymeric delivery systems. A particular need is for systems having greater stability especially for the active agent during the manufacturing process, greater or extended shelf life for the arrays, and/or methods of producing more uniform systems.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method of making an array of microstructures is provided. In an embodiment, the method comprises (a) dissolving or suspending at least one therapeutic agent in a solvent to form a therapeutic agent solution or suspension; (b) dissolving at least one polymer in a solvent to form a polymer solution; (c) mixing the therapeutic agent solution or suspension and the polymer solution or suspension to form a polymer matrix solution or suspension; (d) dispensing the polymer matrix solution or suspension on a mold having an array of microstructure cavities; (e) filling the microstructure cavities in the mold; (f) removing excess solution or suspension polymer matrix on the mold surface; (g) drying the solution or suspension in a chamber having a partial pressure of about 0.01 mTorr-203 Torr at a temperature of about 5-50° C.; (h) drying the solution or suspension at about 5-50° C. to form an array of microstructures; and (i) drying the microstructures under vacuum at about 5-50° C.

In another embodiment, the method comprises (a') dissolving or suspending a therapeutic agent in water to form a therapeutic agent solution or suspension; (b') dissolving at least one polymer in water to form a polymer solution; (c') mixing the therapeutic agent solution or suspension and the polymer solution or suspension to form a polymer matrix solution or suspension; (d') dispensing the polymer matrix solution or suspension on a mold having an array of microstructure cavities; (e') filling the microstructure cavities in the mold; (f') removing excess solution or suspension on the mold surface; (g') drying the solution or suspension in a chamber having relative humidity of about 10-95% at a temperature of about 5-50° C.; (h') drying the solution or suspension at about 5-50° C. to form an array of microstructures; and (i') drying the microstructures under vacuum at about 5-50° C.

In an embodiment, the methods further comprise dispensing a basement or backing layer on the mold surface; and drying the basement or backing layer. In further embodiments, drying the basement or backing layer comprises drying in an oven at about 5-50° C. In yet further embodiments, drying the basement or backing layer comprises drying in an oven at about 5-50° C. In additional embodiments drying the basement or backing layer comprises drying in a compressed dry air box with controlled air flow prior to drying in an oven.

In further embodiments, the chamber of the methods uses convection, conduction, or radiation for drying.

In an embodiment, the mold surface is heated from below using convection, conduction, or radiation to maintain a temperature of the polymer matrix solution or suspension at about 5-50° C.

In an embodiment, the methods further comprise affixing the basement or backing layer to a substrate. In embodiments, the substrate is selected from a pressure sensitive adhesive and a UV cured adhesive. In additional embodiments, the methods further comprise attaching the substrate adhesive to a metal, silicon, and/or polymer layer. In yet further embodiments, the methods comprise using a non-woven or porous film double coated with adhesive to affix the basement or backing layer to the substrate.

In embodiments, the methods further comprise demolding the microstructure tips or microstructure array. In some embodiments, demolding comprises demolding after step (i) or (i'). In other embodiments, demolding comprises demolding after drying the basement or backing layer.

In embodiments, the basement or backing layer is dried by drying the mold from below using conductive or radiative heating In embodiments, prior to step (a) or (a'), the mold is subjected to a surface treatment over at least a portion of its surface prior to dispensing the polymer matrix solution or suspension which makes it easier for the solution or suspension to wet the mold surface. In some embodiments, the surface treatment comprises coating at least a portion of the mold surface with a treatment selected from calcium carbonate, ethyl acetate, a silicone fluid, or oxygen plasma. In further embodiments, prior to step (a) or (a'), the mold is subjected to a treatment which causes it to swell. In yet further embodiments, the methods comprise applying a wetting agent to the mold prior to step (a) or (a'). In certain embodiments, the wetting agent is a silicone polyether surfactant.

In embodiments, step (e) or (e') comprises pressurization of at least about 10 psi above atmospheric. In further embodiments, step (e) or (e') uses soluble gases. In some embodiments, the soluble gas is selected from $CO_2$ and $CH_4$.

In embodiments, one of steps (a) or (b) further comprises dissolving a sugar in the solvent. In other embodiments, one of steps (a') or (b') further comprises dissolving a sugar in the solvent. In yet further embodiments, the methods comprise dissolving a sugar in the polymer matrix solution or suspension after step (c) or (c'). In embodiments, the sugar is selected from sorbitol, sucrose, trehalose, fructose, or dextrose.

In embodiments, one of steps (a) or (b) further comprises dissolving a surfactant in one of the solvents. In other embodiments, one of steps (a') or (b') further comprises dissolving a surfactant in the solvent. In some embodiments, the surfactant is selected from Polysorbate 20 or Polysorbate 80.

In embodiments, wherein one of steps (a) or (b) further comprises dissolving an antioxidant in one of the solvents. In other embodiments, wherein one of steps (a') or (b') further comprises dissolving an antioxidant in the solvent. In some embodiments, the antioxidant is selected from methionine, cysteine, D-alpha tocopherol acetate, EDTA, or vitamin E.

In embodiments, step (b) or (b') comprises dissolving about 10-40% by weight of the polymer in the solvent. In some embodiments, the therapeutic agent is selected from a drug, a small molecule, a peptide or protein, or a vaccine. In embodiments, the therapeutic agent is selected from a drug, a small molecule, a peptide or protein, or a vaccine.

In embodiments, the suspension is a liquid in liquid suspension. In other embodiments, the suspension is a solid in liquid suspension.

Additional embodiments of the present microstructures, arrays, methods, apparatuses, devices, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIGS. 4A-4C are illustrations of shapes of dried microprojections obtained with various methods of preparation.

Figure 1:
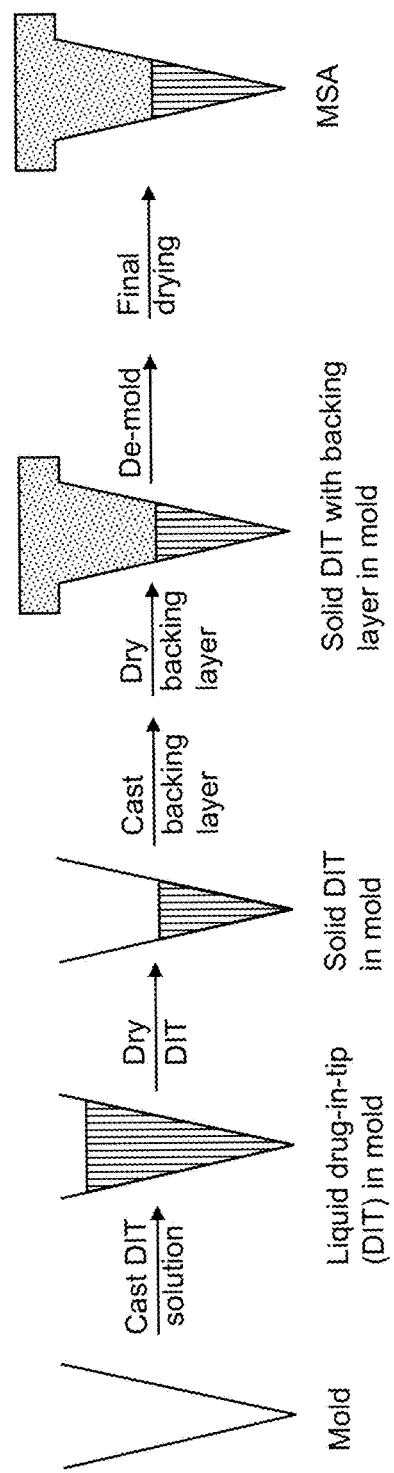
FIG. 1 is an illustration of one embodiment of a method of casting microprojections.

It will be appreciated that the thicknesses and shapes for the various microstructures have been exaggerated in the drawings to facilitate understanding of the device. The drawings are not necessarily "to scale."

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 µm and the range of values less than or equal to 8 µm.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

The terms "microprotrusion", "microprojection", "microstructure" and "microneedle" are used interchangeably herein to refer to elements adapted to penetrate or pierce at least a portion of the stratum corneum or other biological membrane. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

The term "microprotrusion array" for purposes herein is intended to denote a two-dimensional or a three-dimensional arrangement of microprotrusions, microstructures, microprojections, or microneedles. The arrangement may be regular according to a repeating geometric pattern or it may be irregular.

In discussing the applicators and arrays described herein, the term "downward" is sometimes used to describe the direction in which microprotrusions are pressed into skin, and "upward" to describe the opposite direction. However, those of skill in the art will understand that the applicators can be used where the microprotrusions are pressed into skin at an angle to the direction of the earth's gravity, or even in a direction contrary to that of the earth's gravity. In many applicators, the energy for pressing the microprotrusions is provided primarily by an energy-storage member and so efficiency is not much affected by the orientation of the skin relative to the earth's gravity.

In this application reference is often made for convenience to "skin" as the biological membrane which the microprojections penetrate. It will be understood by persons of skill in the art that in most or all instances the same inventive principles apply to the use of microprojections to penetrate other biological membranes such as, for example, those which line the interior of the mouth or biological membranes which are exposed during surgery.

"Biodegradable" refers to natural or synthetic materials that degrade enzymatically, non-enzymatically or both to produce biocompatible and/or toxicologically safe by-products which may be eliminated by normal metabolic pathways.

"Optional" or "optionally" means that the subsequently described circumstance may or may not occur, so that the description includes instances where the circumstance occurs and instances where it does not.

"Substantially" or "essentially" means nearly totally or completely, for instance, 90-95% or greater of some given quantity.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

A typical "microstructure array", "microprojection array", or "microneedle array" comprises microstructures, microprojections, or microneedles projecting from a base or substrate of a particular thickness, which may be of any shape, for example square, rectangular, triangular, oval, circular, or irregular. An array typically comprises a plurality of microstructures, microprojections, or microneedles. The microstructures, microprojections, or microneedles themselves may have a variety of shapes. While an array could be pressed by hand into skin, a variety of devices may be used to hold the array as it is being applied and/or to facilitate in one way or another the process of application of the array to the skin or other biological membrane. Such devices may broadly be referred to as "applicators." Applicators may for example reduce the variations in force, velocity, and skin tension that occur when an array is pressed by hand into the skin. Variations in force, velocity and skin tension can result in variations in permeability enhancement.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also disclosed, as well as the range of values greater than or equal to 1 µm and the range of values less than or equal to 8 µm.

II. METHODS OF MAKING MICROSTRUCTURE ARRAYS

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

Examples of forming various microprojection arrays using different formulations and configurations are provided in Examples 1-3. In one exemplary method, an array is prepared by (a) filling a mold having a plurality of cavities (or at least one cavity) corresponding to the negative of the microstructures with a casting solution or formulation comprising at least one active agent, therapeutic agent, drug, or active pharmaceutical ingredient (API) and one or more excipients in a solvent, (b) removing the solvent, and (c) de-molding the resulting array from the mold. The solvent may be removed by any suitable means including, but not limited, to drying the mold filled with the casting solution in an oven. The casting solution preferably contains at least one an active agent or ingredient, drug, therapeutic agent, or other substance to be delivered to a subject. In one or more embodiments, the microstructures themselves comprise the active ingredient mixed, or dispersed in a polymer matrix, as opposed to having the active ingredient present as a coating on a microstructure or microneedle made of a different, biocompatible material such as a metal. It will be appreciated that the active ingredient may be included within the microstructures themselves as well as in a coating on the microstructure. Typically, excess formulation is scraped or wiped from the mold surface prior to drying. Where the microstructures are not integral with a substrate and/or backing layer, the microstructures are typically affixed to the substrate or backing layer with an adhesive prior to demolding.

The molds used to form the arrays in the methods herein can be made using a variety of methods and materials. Exemplary molds and methods of making molds are described, for example, in U.S. Patent Publication No. 2008/2696585. In one exemplary embodiment, the mold is a negative mold formed from a silicone such as polydimethylsilicone. A negative mold is typically formed by preparing a master microprojection array and casting a liquid mold material over the master array. The mold is allowed to dry and harden, which results in a mold comprising cavities corresponding to the microprojections of the master array. It will be appreciated that the molds suitable for use in the present methods may be prepared according to other methods.

In general, the microprojections have a height of at least about 100 µm, at least about 150 µm, at least about 200 µm, at least about 250 µm, or at least about 300 µm. In general it is also preferred that the microprojections have a height of no more than about 1 mm, no more than about 500 µm, no more than about 300 µm, or in some cases no more than about 200 µm or 150 µm. In embodiments, the microprojections have a height of at least about 50-500 µm. In other embodiments, the microprojections have a height of at least about 100-500 µm, 100-400 µm, 100-300 µm, 100-200 µm, 100-150 µm, 150-500 µm, 150-400 µm, 150-300 µm, 150-200 µm, 200-500 µm, 200-400 µm, 200-300 µm, 300-500 µm, 300-400 µm, or 400-500 µm. It will be appreciated that the microprojections within an array may have a range of heights. The microprojections may have any suitable shape including, but not limited to polygonal or cylindrical. Particular embodiments include pyramidal including a four-sided pyramid, a funnel shape, a cylinder, a combination of funnel and cylinder shape having a funnel tip and a cylindrical base, and a cone with a polygonal bottom, for example hexagonal or rhombus-shaped. Other possible microprojection shapes are shown, for example, in U.S. Published Patent App. 2004/0087992 and in U.S. application Ser. No. 61/745,513 . filed Dec. 21, 2012. Microprojections may in some cases have a shape which becomes thicker towards the base, for example microprojections which have roughly the appearance of a funnel, or more generally where the diameter of the microprojection grows faster than linearly with distance to the microprojection distal end. It will be appreciate that polygonal microprojections may also have a shape which becomes thicker toward the base or where a radius or diameter grows faster than linearly with distance to the microprojection distal end. Where microprojections are thicker towards the base, a portion of the microprojection adjacent to the base, which may be called the "foundation," may be designed not to penetrate the skin.

The microprojections may be spaced about 0-500 µm apart. In specific, but not limiting embodiments, the microprojections are spaced about 0 µm, about 50 µm, about 100 µm, about 150 µm, about 200 µm, about 250 µm, about 300 µm, about 350 µm, about 400 µm, about 450 µm, or about 500 µm apart. The space between the microprojections may be measured from the base of the microprojections (base to base) or from the tip (tip to tip). The spacing of the microprojections may be regular or irregular.

One exemplary master array includes a plurality of diamond shaped projections having a height of about 200 µm, a base of about 70 µm, and spacing between the projections of about 200 µm. In another exemplary embodiment, the master array includes a plurality of hexagonal or other polygonal shaped projections having a height of about 200 µm, a base of about 70 µm, and spacing between the projections of about 400 µm. In yet another embodiment, the master array includes a plurality of cylindrical shaped projections having a height of about 400 µm, a diameter of about 100 µm, and spacing between the projections of about 200 µm. It will be appreciated that the cylindrical shaped projections may have a funnel shaped, pointed, or sharp distal end.

A casting solution is formed by dissolving or suspending one or more therapeutic agents, active agents, drugs, APIs, or other substances to be transdermally delivered and one or more polymers in a solvent to form a polymer matrix solution or suspension. The terms active agent, therapeutic agent, agent, drug, API are used interchangeably herein and discussion or reference to one is intended to include and apply to each and all terms. In one embodiment, the casting solution is formed by dissolving or suspending at least one agent and one or more polymers in an aqueous buffer or solvent to form a solution or suspension comprising the active agent and the polymer. In another embodiment, at least one active agent is dissolved or suspended in a solvent to form an active agent solution or suspension. At least one polymer is separately dissolved in a solvent to form a polymer solution or suspension. The suspension may be a liquid in liquid suspension or a solid in liquid suspension depending on the nature of the active agent and/or polymer. The solvent used for the active agent solution and the polymer solution may be the same or different. The active agent solution and the polymer solution are mixed to form a polymer matrix solution or suspension. It will further be appreciated that a solvent mixture may be used to dissolve or suspend the active agent and/or polymer.

Casting solvents are preferably aqueous solvents. Suitable aqueous solvents include, but are not limited to, water, alcohols (for example, C1 to C8 alcohols such as propanol and butanol), alcohol esters, or mixtures of thereof. In other embodiments, the solvents are non-aqueous. Suitable non-aqueous solvents include, but are not limited to, esters, ethers, ketones, nitrites, lactones, amides, hydrocarbons and their derivatives as well as mixtures thereof. In other non-limiting embodiments, the solvent is selected from acetonitrile (ACN), dimethyl sulfoxide (DMSO), water, or ethanol. It will be appreciated that the choice of solvent may be determined by one or more properties of the active agent and/or polymer. It will further be appreciated that the casting solvent may comprise a mixture of solvents.

Any suitable drug, therapeutic agent, API, or other active agent may be dissolved or suspended in the solvent. The present arrays are suitable for a wide variety of substances or agents. Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In embodiments, the active agent is a biological agent including, but not limited to peptides, polypeptides, proteins, or nucleic acids (e.g. DNA or RNA). In one embodiment, the active agent is a polypeptide such as human parathyroid hormone (e.g. hPTH (1-34)), a protein such as human growth hormone, or an antibody. Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gram icidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. In an embodiment, the vaccine comprises an antigen epitope conjugated on or to a carrier protein. It will be appreciated that vaccines may be formulated with our without an adjuvant. Suitable vaccines include, but are not limited to, vaccines for use against anthrax, diphtheria/tetanus/pertussis, hepatitis A, hepatitis B, *Haemophilus influenzae* type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

In another embodiment, at least a portion of the distal layer comprises an agent suitable for veterinary uses. Such uses include, but are not limited to, therapeutic and diagnostic veterinary uses.

Polymers for use in the methods are typically biocompatible. In one embodiment, at least some of the polymers are biodegradable.

In an embodiment, the polymer is a structure-forming polymer. In an embodiment, the polymer is a hydrophilic water soluble polymer. Suitable polymers are known in the art and described, for example, in U.S. Patent Application No. 2008/0269685. Exemplary biocompatible, biodegradable, or bioerodible polymers include poly(lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer), block copolymers of polyethylene glycol-poly(lactic acid-co-glycolic acid) (PLGA-PEG), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), polysaccharides, polyalcohols, gelatin, alginate, chitosan, hyaluronic acid and its derivatives, collagen and its derivatives, polyurethanes, and copolymers and blends of these polymers. One hydroxyethyl starch may have a degree of substitution of in the range of 0-0.9. An exemplary polysaccharide is dextran including dextran 70, dextran 40, and dextran 10.

The casting solution may further include one or more excipients dissolved or suspended in the buffer or solvent. Suitable excipients include, but are not limited to, one or more stabilizers, plasticizers, surfactants, and/or anti-oxidants.

In one embodiment one or more sugars is added to the casting solution. Sugars can stabilize the active ingredient and/or plasticize at least one of the polymers. Sugars may also be used to affect, moderate, or regulate degradation of the polymer(s). Exemplary sugars include, but are not limited to, dextrose, fructose, galactose, maltose, maltulose, iso-maltulose, mannose, lactose, lactulose, sucrose, and trehalose, and sorbitol. In other embodiments, a sugar alcohol as known in the art is included in the casting solution. Exemplary sugar alcohols include, but are not limited to, lactitol, maltitol, sorbitol, and mannitol. Cyclodextrins can also be used advantageously in microprojection arrays, for example α, β, and γ cyclodextrins. Exemplary cyclodextrins include hydroxypropyl-β-cyclodextrin and methyl-β-cyclodextrin. In other embodiments, where Dextran, hetastarch and/or tetrastarch is used as a polymer in the casting solution, sorbitol may preferably be included in the casting solution. In this embodiment, sorbitol may not only stabilize the active agent, but also plasticize the polymer matrix, which reduces brittleness. The biodegradability or dissolvability of the microprojection array may be facilitated by the inclusion of sugars. Sugars and sugar alcohols may also be helpful in stabilization of peptides, proteins, or other biological active agents and in modifying the mechanical properties of the microprojections by exhibiting a plasticizing-like effect. Where the active agent is a biological agent including, but not limited to, peptides, proteins, and antibodies, one or more sugars or sugar alcohols may be used in the casting solution as a stabilizing agent. The sugar may be added to (i) the therapeutic agent solution or suspension, (ii) the polymer solution or suspension, or (iii) the polymer matrix solution or suspension once (i) and (ii) have been mixed.

One or more surfactants may be added to the casting solution to change the solutions' surface tension and/or reduce the hydrophobic interactions of proteins. Any suitable surfactant as known in the art may be used. Exemplary surfactants include, but are not limited to, emulsifiers such as Polysorbate 20 and Polysorbate 80.

One or more antioxidants may be added to the casting solution. Any suitable antioxidant as known in the art may be used. Exemplary antioxidants include, but are not limited to, methionine, cysteine, D-alpha tocopherol acetate, EDTA, and vitamin E.

Exemplary casting solution formulations are described in Table 1 in Example 1.

The casting solution is dispensed on the mold or into the mold cavities. Where the solution is cast on the mold, the solution is moved into the cavities by any suitable means. In one embodiment, the mold surface with solution thereon is covered to spread the solution or formulation on the mold and at least partially into the cavities. In other embodiments, the solution is spread on the mold without covering. The cavities are filled with the casting solution. In one embodiment, the mold is pressurized, with or without a cover, to move the solution into or further into the cavities of the mold. Pressurization may be accomplished by placing the mold with the casting solution into a pressure vessel as known in the art. Pressurization may involve a pressure of at least about 3 psi, about 5 psi, about 10 psi, about 14.7 psi, about 20 psi, or about 50 psi above atmospheric. In other embodiments, pressurization involves a pressure of at least about 3-50 psi above atmospheric. In other embodiments, pressurization involves a pressure of at least about 3-40 psi, about 3-30 psi, about 3-20 psi, about 3-14.7 psi, about 3-10 psi, about 3-5 psi, about 5-50 psi, about 5-30 psi, about 5-20 psi, about 5-14.7 psi, about 5-10 psi, about 10-50 psi, about 10-30 psi, about 10-20 psi, about 10-14.7 psi, about 20-50 psi, about 20-30 psi, or about 30-40 psi above atmospheric. Excess solution may be wiped or otherwise removed from the mold surface. In another embodiment, a soluble gas is used to move the casting solution into or further into the cavities. Specific, but not limiting, soluble gases are $CO_2$ and $CH_4$.

The mold may be treated prior to dispensing the casting solution to improve dispensing of the casting solution and/or to avoid or reduce the presence of air bubbles. In embodiments, the mold, or portions thereof, is treated to improve the ability of the casting solution to wet the mold. Suitable treatments are known in the art and described, for example, in U.S. Patent Publication No. 2008/0269685, which is incorporated herein in its entirety. In addition, or separately, the casting solution may include ingredients to prevent, reduce, or minimize bubbling. One exemplary ingredient is an anti-foaming agent. Another embodiment of a surface treatment includes coating at a least a portion of the mold with a substance that improves the ability of the casting solution or suspension to wet the mold surface. In non-limiting embodiments, at least a portion of the mold surface is coated with at least one of calcium carbonate, ethyl acetate, a silicone fluid, or oxygen plasma.

The mold with liquid casting solution is then dried using one or multiple primary drying steps based on physiochemical properties of the formulations including, but not limited to, viscosity, solid content, surface interaction between the formulation and the mold, etc. Drying causes volume change in the formulation and hence the movement of the formulation down to the distal end of the mold cavity. Surface drying causes the formulation to "pin" to the walls of the mold cavity thereby arresting the downward movement of the formulation. Multiple primary drying steps may be useful where pinning would occur early in the drying process.

In one embodiment, multiple and/or controlled drying steps are used to remove excess solvent and/or dry the microprojections. In one preferred embodiment, the methods include a two step primary drying. The primary drying should have controlled and optimal drying conditions which ensures the dried solid in the mold has a desirable geometry and morphology and/or the drying conditions do not affect the stability of the active agent during drying. The first step is a slow drying method in which the mold with casting solution is dried under controlled humidity. In another embodiment, the casting solution is dried in a chamber having a controlled partial pressure of the evaporate. The slow drying step has two primary functions: 1) to prevent or slow down skin formation and/or 2) prevent or slow down pinning of the formulation on the mold interface. In one embodiment, the mold is slow dried over a period of about 1-30 minutes or about 5-30 minutes. In embodiments, the mold is dried over a period of at least about 1-60, 1-45, 1-25, 1-20, 1-15, 1-10, 1-5, 5-60, 5-45, 5-25, 5-20, 5-15, 5-10, 10-60, 10-45, 10-30, 10-25, 10-20, 10-15, 15-60, 15-45, 15-30, 15-25, 15-20, 20-60, 20-45, or 20-30 minutes. In specific, but not limiting embodiments, the mold is dried over a period of at least about 1, 5, 10, 15, 20, 25, 30, 40, 45 minutes or an hour. Typically, the mold is placed in a controlled humidity chamber. Preferably, the humidity in the chamber is controlled from at least about 10% to about 95% relative humidity (RH). In embodiments, the humidity in the chamber is controlled at about 75%-95%, about 75%-90%, about 75%-85%, about 75%-80%, about 80%-95%, about 80%-90%, or about 90%-95%. In specific embodiments, the humidity in the chamber is at least about 10%, about 20%, about 30%, about 40%, about 50%, about 60%, about 75%, about 80%, about 85%, about 90%, about 95%, or greater. It will be appreciated that relative humidity may be considered where the solvent is water. In other embodiments, partial pressure in the chamber is controlled from about 0.01 mTorr to about 230 Torr. In one specific embodiment, where the solvent is DMSO (10%), the partial pressure is about 0.01 mTorr when using a temperature of about 10° C. When using a more volatile solvent such as ethanol, a higher partial pressure may be useful. For example, for 90% ethanol as the solvent, the partial pressure is about 230 Torr when using a temperature of about 50° C. The air convection in the chamber may also be controlled with no convection, low air convection, or high convection. The temperature in the chamber is controlled, typically to between about 5-50° C. The chamber may use convection, conduction, or radiation. In one embodiment, the chamber is at room temperature. The second drying step comprises placing the mold in an oven such as an incubator oven at about 5-50° C. Exemplary primary drying conditions are described in Table 2 in Example 1. Particularly where the active ingredient is macromolecular or biological, it may be desirable to avoid extensive use of heat in the solvent removal steps because of the possibility of denaturation of the active agent. In embodiments, it is preferable that the temperature be maintained below about 100° C. (except perhaps for brief periods). In embodiments, the temperature is maintained below about 90° C., below about 85° C., below about 80° C., below about 50° C., below about 40° C., below about 45° C., below about 37° C., below about 35° C., or below about 30° C. In other embodiments, the temperature is maintained between about 5-40° C., 5-30° C., 5-25° C., 10-50° C., 10-40° C., 10-30° C., 10-25° C., 10-20° C.

Figure 4C:
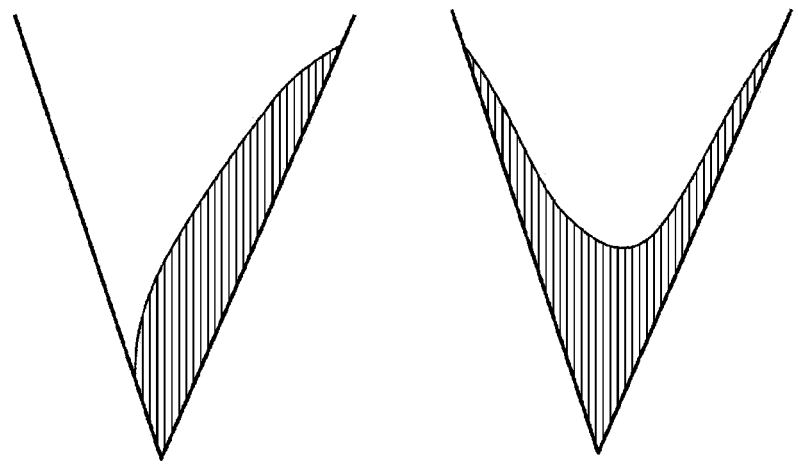
Figure 4C:
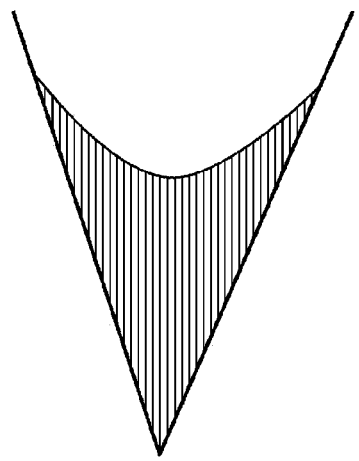
Figure 5:
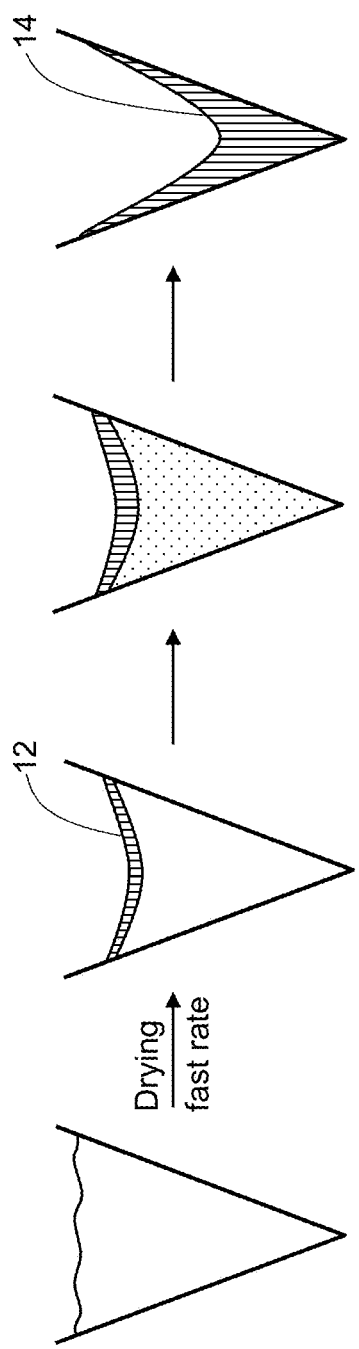
FIG. 5 is an illustration of one method of forming microprojections.

Depending on the properties of the casting layer liquid formulation and/or the methods of drying, the shape and/or morphology of the dry microprojection in the tip can be significantly affected. As seen in FIG. 4A, the formulation may dry to one side of the cavity resulting in the solid active agent formulation being uneven in the tip of the resulting microprojection. As seen in FIG. 4B, the formulation may dry with a high meniscus. A high meniscus dried formulation may result when the liquid formulation is dried at a fast rate as shown in FIG. 5. As shown in FIG. 5, liquid formulation is placed in the cavities and dried at a fast rate or speed. A dried skin of formulation 12 forms at the proximal surface or air interface surface within the cavity. The remaining formulation dries only after further drying steps, that is not in the primary or DIT drying step. The resulting configuration has a high meniscus 14, is less dense, and has a high surface volume. Both of these geometries can affect the use of the resulting microprojection array. For example, the degradation rate and delivery for degradable microprojections may be affected. For a microprojection with the agent formulation concentrated on one side, a smaller area for degradation of the active agent formulation will be presented as the backing layer fills the other side of the cavity. This can slow degradation and delivery of the active agent. Conversely, a tip having a high meniscus as seen in FIG. 4B may result in a faster degradation rate and delivery of the active agent. A high meniscus presents a higher surface area for degradation of the active agent formulation. A preferred dried shape for the active agent formulation is shown in FIG. 4C which shows a tip with minimal meniscus and uniform, lowest solid volume.

Figure 3A:
FIGS. 3A-3C are images of microprojection arrays prepared under humidity controlled conditions (FIG. 3A) and dried without humidity control (FIGS. 3B-3C) after dissolution.
Figure 3B:
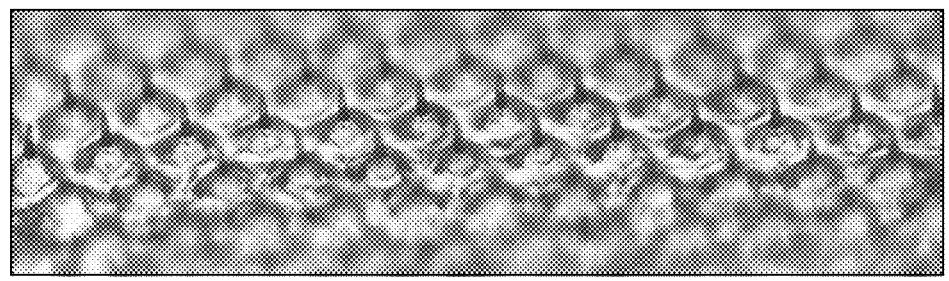
Figure 3C:
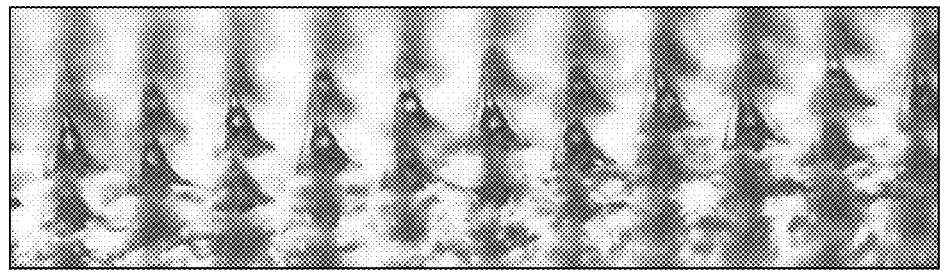

Without being limited as to theory, controlling the humidity during primary drying is believed to prevent the formation of a solid film or skin at the proximal surface of the casting solution. Formation of the skin results in pinning on the mold surface while the bulk of the casting solution remains in liquid form until further drying steps are taken. The resulting microstructures have a high meniscus for the DIT portion as shown in FIG. 3B. As described in Example 6 and shown in FIGS. 3A-3C, controlling humidity at least during the primary drying step results in microstructures that dissolve evenly. FIG. 3A shows the stumps of MSA projections formed without humidity control in the primary drying step after immersion in an aqueous medium for about 10 minutes. These microstructures had a DIT portion with a high meniscus. When the DIT portion degrades after application of the microstructure array, the resulting stumps appear to be thin, pointy needles. FIG. 3B shows the stumps of MSA projections formed without humidity control in the primary drying step after immersion in an aqueous medium for about 10 minutes. The DIT of these microstructures dried toward one side of the mold, leaving the other side empty to be filled by the backing layer. When the DIT portion degrades after application of the microstructure array, the resulting stumps appear to be shaped like a fingernail from the remaining non-dissolvable backing layer. In contrast, the stumps of the MSA projections are evenly dissolved (FIG. 3C).

In another preferred embodiment, the mold with the liquid casting solution is dried from beneath, under or below the mold. It will be appreciated that the casting solution may be dried from substantially beneath, under or below the mold. This method has the same benefits as the drying method described above. In addition, the under method of drying has the additional benefit of reducing time necessary for drying. In embodiments, the microstructure formulation is dried from underneath for 5-30 minutes. In other embodiments, the formulation is dried from underneath for 5-25 minutes, 5-20 minutes, 5-15 minutes, 5-10 minutes, 10-25 minutes, 10-20 minutes, 10-15 minutes, 15-25 minutes, 15-20 minutes, or 20-25 minutes. In specific embodiments, the formulation is dried from underneath for about 5, 10, 15, 20, 25, or minutes. In embodiments, the mold is heated to maintain or substantially maintain the temperature of the formulation at about 5-50° C. The formulation may be dried from below using conductive and/or radiative heating. In embodiments, the mold surface is heated from below. It will be appreciated that the parameters including, but not limited to, temperature, time, and equipment as described above are contemplated and intended to apply to the under drying method.

Figure 6:
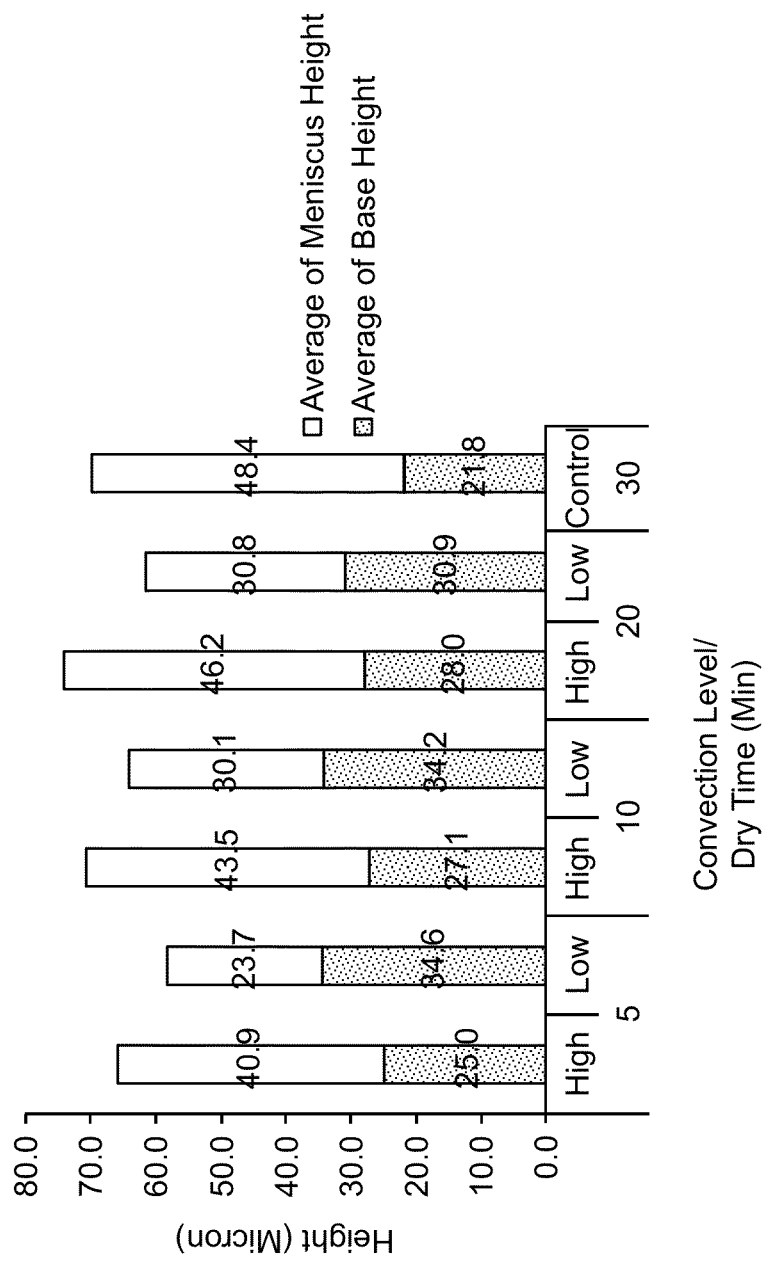
FIG. 6 is a plot of the average meniscus and base height in microns of microstructures for various convection drying conditions.
Figure 7:
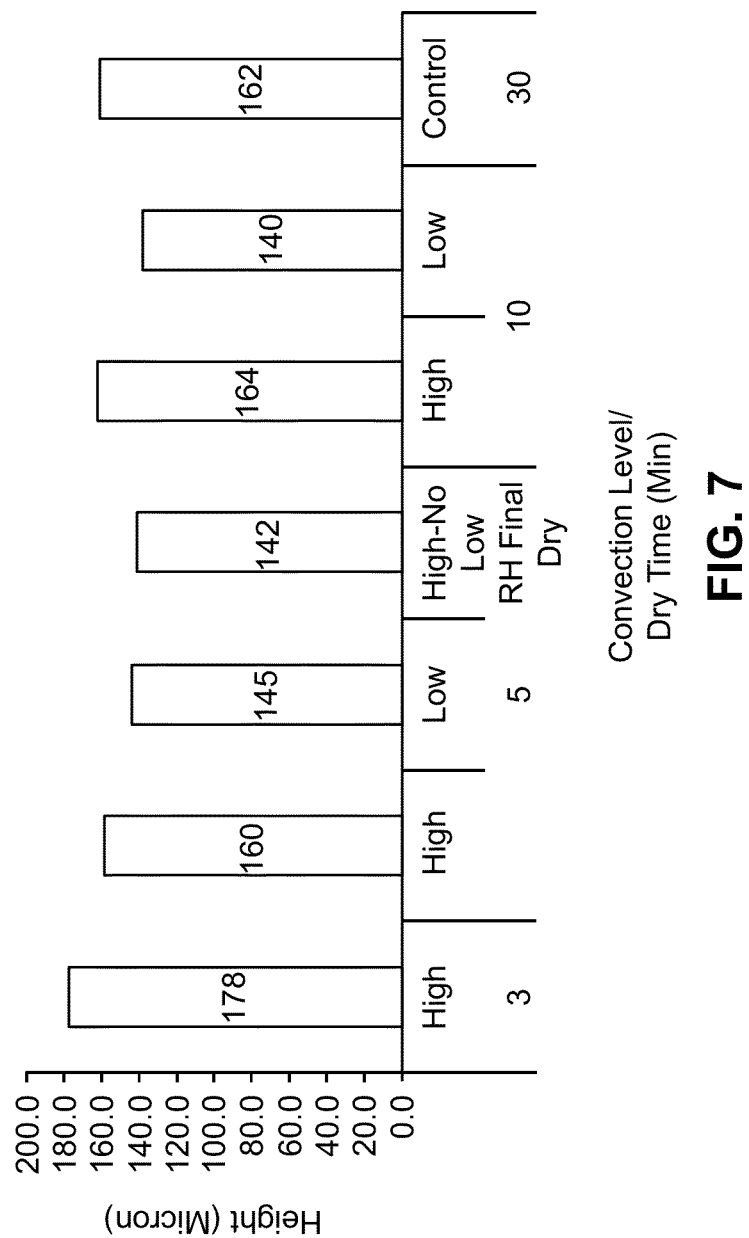
FIG. 7 is a plot of the meniscus height in microns for various convection drying conditions.
Figure 9:
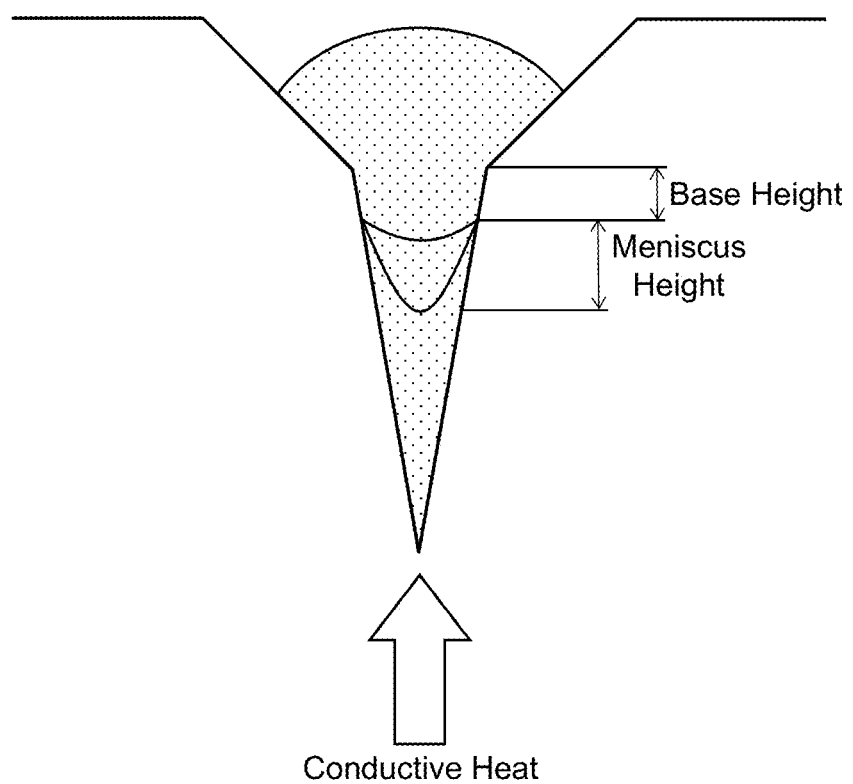
FIG. 9 is an illustration of a formulation dispensed in a mold showing a meniscus for a microstructure after drying.

As described in Example 5 and shown in FIGS. 6-7, drying the formulations from under the mold results in microstructures having a minimal meniscus and uniform, lowest solid volume. FIG. 6 is a comparison of microstructures dried from beneath the mold using high or low convection and dried for 5, 10, or 20 minutes as compared to microstructures dried in accord with Example 3 for 30 minutes. Guidelines for the base height and meniscus measurements are shown in FIG. 9. As seen in FIG. 6, the total height, base height and meniscus height was similar to or less than the control. The efficacy of the drying process may be inversely correlated to the height of the resulting meniscus. Here the meniscus for each of the microstructures formed using the under drying method is less than the controlled humidity method disclosed above. Using an under drying method results in comparable or improved meniscus formation for the microstructures after drying for 5-20 minutes. Thus, using under drying allowed for a drying time of less than 20% of the time used for the controlled humidity method. As also seen in FIG. 6, the microstructures formed using a high convection had a similar meniscus to microstructures formed using low convection. Thus, the under drying method provides tolerability to high convection during drying.

FIG. 7 shows the meniscus height (using a base height of 0) for microstructures formed according to Example 4. As seen in FIG. 7, the meniscus height was similar to or lower than the control after drying for 3, 5, or 10 minutes. The microstructures formed using high convection had a similar meniscus to microstructures formed using low convection.

An additional microstructure ("high—No low RH Final Dry") is dried from under the mold for 5 minutes using high relative humidity and low convection. The mold is not additionally dried under vacuum. The microstructure is dried in 5 minutes (total time) and has a meniscus that is similar to or lower than the control. Under drying of the mold allows for an improvement/reduction in the drying time required.

In one embodiment, an optional backing layer, base layer, or basement is further cast on the mold. A liquid backing formulation is dispensed on the mold or into the cavities. The liquid backing formulation is typically prepared by dissolving or suspending one or more polymers in a suitable solvent. In a preferred embodiment, the one or more polymers are biocompatible. Typically, but not always, the polymers are non-biodegradeable. In another embodiment, the backing formulation may comprise one or more biodegradable and/or non-biodegradable polymers. Suitable biodegradable polymers are described above. Suitable non-biodegradable polymers are known in the art and include, but are not limited to, am phiphilic polyurethanes, polyether polyurethane (PEU), polyetheretherketone (PEEK), poly (lactic-co-glycolic acid) (PLGA), polylactic acid (PLA), polyethylene terephthalate, polycarbonate, acrylic polymers such as those sold under the trade name Eudragit®, polyvinylpyrrolidones (PVP), polyamide-imide (PAI), and/or co-polymers thereof. Further suitable polymers are described in U.S. Pat. No. 7,785,301, which is incorporated herein in its entirety. In another embodiment, the backing layer is an adhesive layer. Exemplary polymer backing layer formulations are described in Table 2 in Example 2. One suitable adhesive is the Dymax® 1187-M UV medical device adhesive. It will be appreciated that any biocompatible adhesive is suitable for use with, in and/or as the backing layer. This layer may also be a nonwoven or porous film double coated with pressure sensitive adhesive. Liquid backing formulations may be moved into the cavities by the same or similar methods as for the active agent casting solution. Where a liquid backing layer formulation is used, the solvent of the backing layer formulation is removed by a drying process. The drying conditions for drying the backing layer should be controlled so that the backing layer solvent can be removed effectively without affecting the stability of an active agent and/or to properly form (e.g. uniform) the backing layer. In one embodiment, the mold is placed into a compressed dry air (CDA) box under controlled air flow and then placed in an oven at about 5-50° C. In further embodiments, the mold is placed in the oven at a temperature of about 5-50° C. In embodiments, the temperature of the CDA and/or oven is about 5° C., about 10° C., about 20° C., about 30° C., about 40° C., about 45° C., or about 50° C. In embodiments, the temperature of the CDA and/or oven is about 5-45° C., 5-40° C., 5-30° C., 5-20° C., 5-15° C., 5-10° C., 10-50° C., 10-45° C., 10-40° C., 10-30° C., 10-20° C., 0, 10-15° C., 15-50° C., 15-45° C., 15-40° C., 15-30° C., 15-20° C., 20-50° C., 20-45° C., 20-40° C., 20-30° C., 30-50° C., 30-45° C., 30-40° C., 30-45° C., 40-50° C., 40-45° C., or 45-50° C. In embodiments, the oven uses convection, conduction, or radiation for drying. In another embodiment, the mold is placed in an oven at about 5-50° C. without prior time in a CDA box. In embodiments, the mold is placed in the CDA and/or oven for at least about 0-120 minutes, about 30-120 minutes, about 30-90 minutes, about 30-60 minutes, about 30-45 minutes, about 45-120 minutes, about 45-90 minutes, about 45-60 minutes, about 60-120 minutes, about 60-90 minutes, about 90-120 minutes, or longer. Residual solvents in the backing layer can be measured to determine the effectiveness of solvent removal under different drying conditions. Examples of suitable drying conditions for the backing layer are summarized in Table 4 in Example 2. The backing layer connects and/or supports the microprojection tips.

Figure 8:
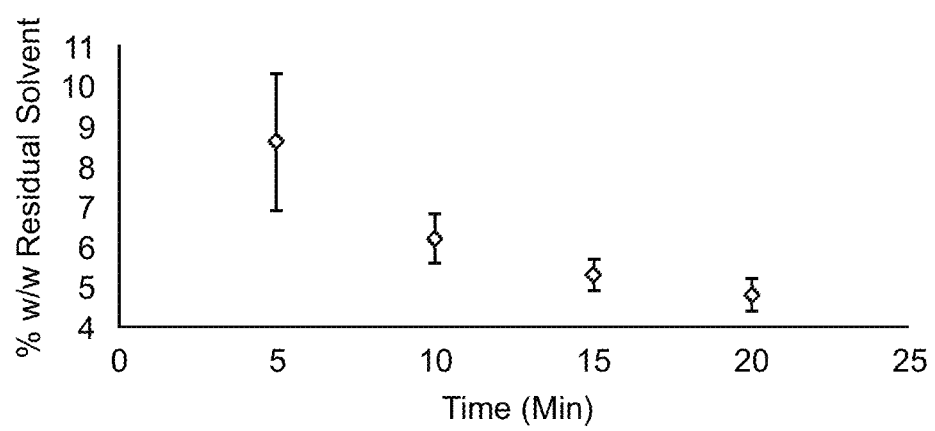
FIG. 8 is a plot showing the effect of lower region drying time on residual solvent showing the % w/w residual solvent (acetonitrile) over time in minutes.

Under drying of the mold allows for an improvement/ reduction in the drying time required for the backing layer, base layer or basement. As described in Example 5, the backing layer is also dried from beneath, under or below. Drying the backing layer also reduces the time required to dry the backing layer. Using the under drying method, the backing layer may be dried in under 20-30 minutes. In embodiments, the microstructure formulation is dried from underneath for 5-45 minutes or 5-30 minutes. In other embodiments, the formulation is dried from underneath for 5-25 minutes, 5-20 minutes, 5-15 minutes, 5-10 minutes, 10-25 minutes, 10-20 minutes, 10-15 minutes, 15-25 minutes, 15-20 minutes, or 20-25 minutes. In specific embodiments, the backing layer formulation is dried from underneath for about 5, 10, 15, 20, 25, or 30 minutes. In embodiments, the mold is heated to maintain or substantially maintain the temperature of the backing layer formulation at about 5-50° C. The formulation may be dried from below using conductive and/or radiative heating. In embodiments, the mold surface is heated from below. It will be appreciated that the parameters including, but not limited to, temperature, time, and equipment as described above are contemplated and intended to apply to the under drying method. FIG. 8 shows a drying curve for a backing layer dried by heating from below. As seen in FIG. 8, the % w/w residual solvent is less than 9% after drying for 5 minutes and less than 5% w/w after 20 minutes. The solvent content drops to near asymptotic (less than 5%) after 20 minutes of heating. In comparison, a backing layer dried using convective heating had a residual solvent content of 2.5% w/w after 120 minutes.

FIG. 1 is an illustration of the method of forming microstructures having a drug-in-tip (DIT) and a backing layer. A liquid DIT solution is cast on a mold having at least one cavity in the shape desired for the microstructures. The liquid DIT is dried under controlled conditions to remove the solvent resulting in a solid DIT layer in the bottom or distal end of the cavity. A backing layer is cast such that the remaining space in the cavity is filled and, optionally, a layer of backing layer formulation extends between the cavities. The backing layer is dried such that the resulting array has a backing layer with a plurality of microstructures extending at an angle from the backing layer. The backing layer with attached microstructures is demolded and undergoes a final drying step to form the microstructure array (MSA). It will be appreciated that the MSA may be demolded prior to undergoing the final drying step.

The microprojections may be positioned on a base or substrate to form the array. The substrate may be in addition to or used with a backing layer. The microprojections may be attached to the substrate by any suitable means. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax. It will be appreciated that any medical device adhesive known in the art would be suitable. In one embodiment, the substrate is a breathable nonwoven pressure sensitive adhesive. The substrate is placed on the backing layer where present or a proximal surface of the microprojections.

The substrate is adhered or attached to the microprojections. In another embodiment, the substrate is a UV cured adhesive in a polycarbonate film. The UV adhesive is dispensed on the top of the backing layer or the proximal surface of the microprojections, covered with a polycarbonate (PC) film to spread the adhesive and cured using a UV Fusion system. In one embodiment a UV curing dose is about 1.6 J/cm$^2$. After the substrate is attached or adhered to the microprojections, the microprojection array is removed from the mold. It will be appreciated where the array includes a backing layer the substrate is attached or adhered to the backing layer as described above for the microstructures.

As described in Example 3, a polymer matrix is cast in a mold and dried with a primary drying method to form a proximal layer as described in Example 1 and above. A backing layer is cast onto the proximal layer as described in Example 2 and above. A UV adhesive is dispensed on the backing layer, covered with a polymer film such as a 5 mL PC film and the UV adhesive is cured using a UV Fusion system with a UV curing dose of 1.6 J/cm$^2$.

The backing layer may also be dried from beneath, under, or below the mold.

Cast microprojection arrays are removed from the mold by any suitable means. In one embodiment, the microprojection array is removed from the mold by using a de-mold tool which has a rolling angle of about 1-90 degrees from the plane. A double-sided adhesive is placed on the back of microprojection array with one side for adhering to the array and the other side for adhering to the de-mold tool. The array is removed from the mold by gently rolling the de-mold tool over the adhesive on the back of the array with a slight the rolling angle, such as about 1-90 degrees, preferred about 5-75 degrees, more preferred about 10-45 degrees. The microprojection array is then gently peeled off from the de-mold tool. The arrays may be demolded after drying the backing layer or after a final drying step.

Before or after the microprojection array is removed from the mold a final drying step may be performed under vacuum. The final drying may be at room temperature or at an elevated temperature. In embodiments, the final drying is at about 5-50° C. In embodiments, the final drying is at about 5° C., at about 10° C., at about 20° C., at about 25° C., at about 35° C., at about 40° C., at about 45° C., or at about 50° C. Further suitable temperatures and ranges are described above with reference to drying the backing layer. In embodiments, the final drying is from about 1-24 hours or longer, from about 4-20 hours, from about 6-10 hours, from about 8-16 hours, from about 8-12 hours, from about 8-10 hours, from about 10-12 hours, from about 10-16 hours, from about 12-16 hours or longer. In other embodiments, the final drying step is overnight. Exemplary final drying steps are described in Table 5 in Example 3.

After the microprojection array is removed from the mold, it may be cut to an appropriate size and/or shape. In one embodiment, the microprojection array is die cut with an 11 or 16 mm punch.

Figure 2:
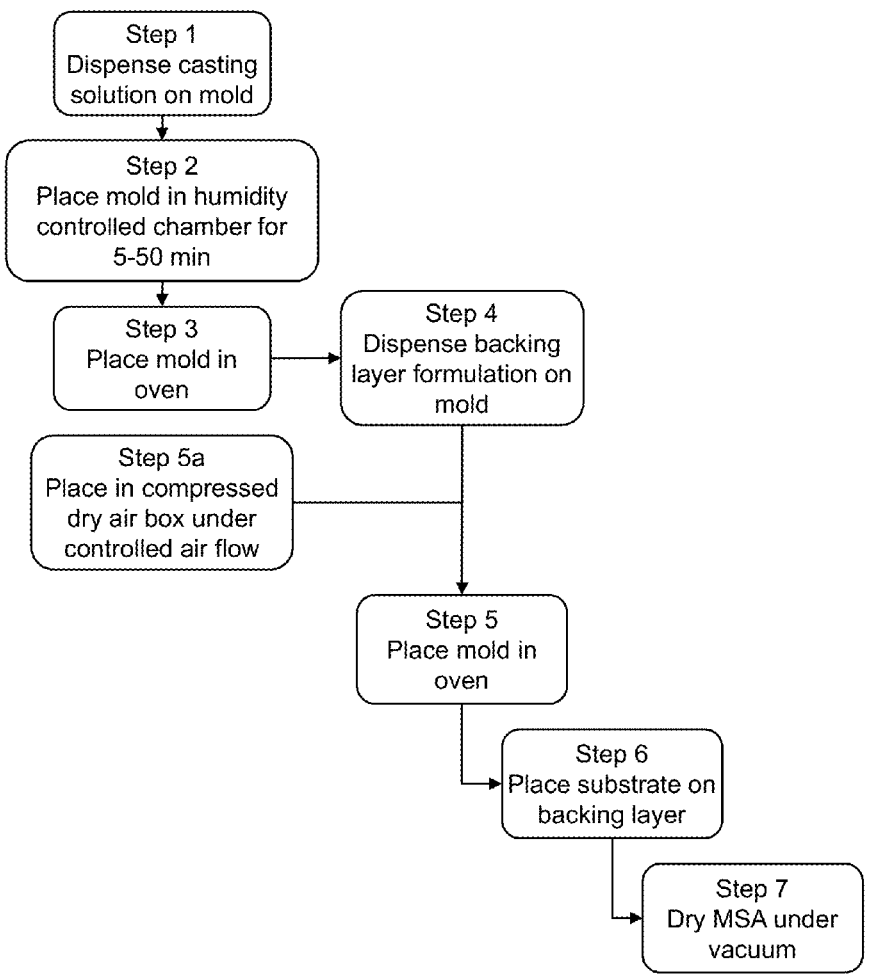
FIG. 2 is a flowchart of one method of forming a microprojection array.

FIG. 2 is a flowchart showing one exemplary method of forming a microstructure array having a backing layer and a substrate using two step primary drying. In step 1, a casting solution is dispensed on a mold or into cavities in the mold. The primary drying includes first placing the mold in a humidity controlled chamber at or near room temperature or at an elevated temperature for about 5-30 minutes (step 2). Preferably, the humidity is controlled at about 50%-90% RH. The mold is then placed in an incubator or oven for about 20-30 minutes (step 3). The temperature in the oven is typically slightly above room temperature (e.g. about 32° C.). A backing layer is dispensed on the mold or into the cavities such that the backing layer contacts a proximal surface of the dried or partially dried active agent formulation in the cavity distal ends (step 4). The backing layer connects and supports the active agent layer. Optionally, the mold is placed in a compressed dry air box under controlled air flow for a suitable period of time (step 5a). The mold is placed in a convection oven at about 45° C. for about 30-120 minutes (step 5). A substrate is dispensed or placed on a proximal surface of the backing layer (step 6) and the resulting microstructure array is dried under vacuum overnight or about 6-18 hours (step 7). It will be appreciated that any one of or all of steps 4-7 may be optional depending on whether the microstructure array includes a backing layer and/or substrate.

III. MICROSTRUCTURE ARRAYS

General features of microstructure arrays suitable for use in the instant arrays and methods are described in detail in U.S. Patent Publication No. 2008/0269685, U.S. Patent Publication No. 2011/0006458, and U.S. Patent Publication No. 2011/0276028, the entire contents of which are explicitly incorporated herein by reference.

The microstructure arrays are preferably stable both during the fabrication process as described above and have a stable shelf life. Short-term stability of the arrays may be evaluated by storing the arrays at various temperatures and/or humidities and analyzing monomer content, composition purity, and deamidation of proteins by SEC-HPLC, RP-HPLC, and IEX-HPLC, respectively at specific time points as described in Example 8. The liquid casting solution or formulation is preferably stable during the fabrication process, which typically lasts a few hours. Preferably, the liquid casting solution is stable for a period of 30 minutes to 6 hours. In non-limiting embodiments, the liquid casting solution is stable for a period of at least from 30 minutes to 1 hour, from 30 minutes to 2 hours, from 30 minutes to 3 hours, from 30 minutes to 4 hours, from 30 minutes to 5 hours, from 1-6 hours, from 1-5 hours, from 1-4 hours, from 1-3 hours, from 1-2 hours, from 2-6 hours, from 2-5 hours, from 2-4 hours, from 2-3 hours, from 3-6 hours, from 3-5 hours, from 3-4 hours, from 4-6 hours, from 4-5 hours, or from 5-6 hours. In specific, but not limiting embodiments, the liquid casting solution is stable for at least about 30 minutes, about 45 minutes, about 1 hour, about 2 hours, about 3 hours, about 4 hours, about 5 hours, about 6 hours, or longer. The microstructure arrays are preferably stable for at least about one day when stored at about room temperature (e.g. about 25° C.). In other embodiments, the arrays are preferably stable for at least about 1 week when stored at about 5° C. In other embodiments, the arrays are stable when stored at an elevated temperature (e.g. about 40° C.) for at least about 1-12 weeks, about 1-16 weeks, or about 1-32 weeks. In other embodiments, the arrays are stable when stored at about 5° C. for at least about 1-52 weeks or 1-156 weeks. It will be appreciated that the shelf-life may vary depending on the storage temperature. In embodiments, the arrays are stable when stored at about 5° C. for at least about 1-156 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In embodiments, the arrays are stable when stored at about 40° C. for at least about 1-26 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In other embodiments, the arrays are stable when stored at about 25° C. for at least about 1-14 days. In further embodiments, the arrays are stable when stored at about 25° C. for at least about 1-12 weeks, about 1-16 weeks, about 1-104 weeks, or about 1-156 weeks. In specific, but not limiting, embodiments, the arrays are stable when stored at about 5° C. for at least about 5 days, at least about 1 week, at least about 2 weeks, at least about 4 weeks, at least about 5 weeks, at least about 6 weeks, or longer. In embodiments, the arrays are stable when stored at about 25° C. for at least about 1-2 days, about 1-5 days, about 1-7 days, about 1-10 days, about 2-5 days, about 2-7 days, about 2-10 days, about 2-14 days, about 3-5 days, about 3-7 days, about 3-10 days, about 3-14 days, about 5-14 days, about 5-10 days, about 5-14 days, or about 10-14 days. In specific, but not limiting, embodiments, the arrays are stable when stored at about 25° C. for at least about 12 hours, at least about 1 day, at least about 2 days, at least about 3 days, at least about 4 days, at least about 5 days, at least about 6 days, at least about one week, or longer. Stability is typically monitored by measuring the purity of the active agent in the array after storage as compared to an array before storage (time=0). In embodiments, the array has a purity of at least about 80-100%, about 85-100%, about 90-100%, about 95-100%, about 80-95%, about 85-95%, about 90-95% about 80-90%, about 85-90% or about 80-85% after storage. In non-limiting embodiments, the array has a purity of at least about 80%, about 85%, about 90%, about 92%, about 93%, about 95%, about 96%, about 97%, about 98%, about 99%, or about 100% after storage.

Where the active agent is a protein, Methionine-oxidation (Met-oxidation) is preferably less than or equal to 1-20% after storage for about 1-6 weeks at about 5° C.-40° C. In embodiments Met-oxidation is less than about 1-10%, about 1-5%, about 1-6%, about 2-3%, about 2-4%, about 2-5%, 2-6%, about 3-5%, or about 3-6%. In specific, but not limiting, embodiments, Met-oxidation is less than about 1%, about 2%, about 3%, about 4%, about 5%, about 6%, or about 10%.

As described in Example 8, MSAs were prepared using hPTH (1-34) as the active agent. The MSA was dried at 35-45° C. for about 90-150 minutes after application of the backing layer. In some embodiments, the MSAs were additionally dried at 45° C. for about 30 minutes. Methionine was added as an antioxidant for three of the MSAs. hPTH purity was extremely stable for all backing layer drying conditions. The area % purity of hPTH in the microstructures was greater than 99% for each of the MSAs.

The microstructure arrays should have sufficient mechanical strength to at least partially penetrate the stratum corneum or other membrane surface of a subject. It will be appreciated that different mechanical strength will be required for application at different sites. One method for assessing mechanical strength is a skin-penetration efficiency (SPE) study as described in Example 7. Preferably, the arrays have a SPE of about 50-100%. In other embodiments, the arrays have a SPE of about 50-80%, about 50-85%, about 50-90%, about 50-95%, about 60-80%, about 60-85%, about 60-90%, about 60-95%, about 60-100%, about 75-80%, about 75-85%, about 75-90%, about 75-95%, about 75-100%, about 80-85%, about 80-90%, about 80-95%, about 80-100%, about 90-95%, and about 90-100%. In specific, non-limiting, embodiments, the arrays have a SPE of about 50%, 60%, 70%, 75%, 80%, 85%, 90%, 95%, 99%, and 100%.

Preferably, at least about 50-100% of the active agent is delivered by the MSAs described herein. Delivery efficiency may be determined by preparing the MSA and applying the MSA in vivo or in vitro as described in Example 7. In embodiments, the MSA has a delivery efficiency of at least about 50-60%, about 50-70%, about 50-75%, about 50-80%, about 50-90%, about 50-95%, about 50-99%, about 60-70%, about 60-75%, about 60-80%, about 60-90%, about 60-95%, about 60-99%, about 70-75%, about 70-80%, about 70-90%, about 70-95%, about 70-99%, about 75-80%, about 75-90%, about 75-95%, about 75-99%, about 80-90%, about 80-95%, about 80-99%, about 90-95%, about 90-99%, or about 95-99%.

IV. METHODS OF USE

The methods, kits, microstructure arrays and related devices described herein may be used for treating any condition. It will be appreciated that the microstructure arrays may be used with any appropriate applicator including the applicator described in U.S. Publication No. 2011/0276027, as well as those described in U.S. Application No. 61/778,274 and U.S. Application No. 61/801,904, each of which are incorporated herein in their entirety.

V. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Casting Microstructure Arrays

Liquid casting formulations are prepared by dissolving an active pharmaceutical ingredient (API), polymer, sugar, polysorbate 20, and EDTA in a water soluble solvent as shown in Table 1.

TABLE 1

Liquid Casting Solution Formulations

| Polymer | | Sugar | | API | | PS20 | EDTA |
|---|---|---|---|---|---|---|---|
| Type | Wt % | Type | Wt % | Type | Wt % | Wt % | mg/mL |
| Dextran 70 | 14 | Sorbitol | 5 | PTH | 1.8 | NA | NA |
| Dextran 70 | 10 | Sorbitol | 4 | PTH | 1.8 | NA | NA |
| Tetrastarch | 14 | Sorbitol | 7 | PTH | 1.8 | NA | NA |
| Tetrastarch | 10 | Sorbitol | 5 | PTH | 1.8 | NA | NA |
| Hetastarch | 14 | Sorbitol | 7 | PTH | 1.8 | NA | NA |
| Hetastarch | 10 | Sorbitol | 5 | PTH | 1.8 | NA | NA |
| Dextran 40 | 14 | Sorbitol | 5 | PTH | 1.8 | NA | NA |
| Dextran 70 | 14 | Sorbitol | 5 | PTH | 2.8 | NA | NA |
| PVA | 14 | Sucrose | 5 | PTH | 2.8 | NA | NA |

About 75 μl of liquid casting solution formulation is dispensed on a silicone mold, covered with a 22 mm×30 mm glass cover slip to spread the formulation on the mold, and then pressurized at 50 psi for 1 minute.

The formulation is wiped and the mold placed in a controlled humidity chamber for a slow drying step as shown in Table 2. The mold is then placed in an incubator oven at 32° C. for 30 minutes.

TABLE 2

Primary Drying Conditions

Slow Drying Conditions

| Humidity (% RH) | Time (min) | Convection | Dry at 32° C. (min) |
| --- | --- | --- | --- |
| NA | 0 | NC | 30 |
| 75 | 5 | NC | 30 |
| 75 | 15 | NC | 30 |
| 85 | 30 | Low | 30 |
| 85 | 30 | High | 30 |
| NA | 0 | NC | 30 |
| 75 | 15 | NC | 30 |
| NA | 0 | NC | 30 |
| 75 | 15 | NC | 30 |
| NA | 0 | NC | 30 |
| 75 | 15 | NC | 30 |

NC is not controlled

Example 2

Polymeric Solutions for Casting Backing Layers of Arrays

Different polymeric solutions may be used for casting a basement or backing layer for the microstructure arrays. Liquid formulations for a backing layer are prepared by dissolving one or more polymers in a solvent or solvent mixture at or about room temperature with a polymer concentration of about 10-40% by weight. Liquid formulations for casting a backing layer are prepared according to Table 3.

TABLE 3

Liquid Backing Layer Formulations

| Polymer | | Solvent | |
| --- | --- | --- | --- |
| Type | Wt % | Type | Wt % |
| Eudragit EPO 100 | 20 | Ethanol/IPA (3:1) | 80 |
| Eudragit EPO 100 | 30 | Ethanol/IPA (3:1) | 70 |
| Eudragit EPO 100/PVP (1:1) | 20 | Ethanol/IPA (3:1) | 80 |
| PLGA (75/25) | 10 | Ethyl acetate | 90 |
| PLGA (75/25) | 15 | Ethyl acetate | 85 |
| PLGA (75/25) | 25 | Acetonitrile | 75 |
| PLGA (75/25) | 35 | Acetonitrile | 65 |
| PLGA (65/35) | 20 | Acetonitrile | 80 |
| PLGA (65/35) | 30 | Acetonitrile | 70 |
| PLA | 20 | Acetonitrile | 80 |

Liquid backing layer formulation is dispensed on the mold. A thin film is cast by wiping the backing layer formulation. The mold is dried according to Table 4 which shows primary drying conditions as well as conditions for drying the backing layer.

TABLE 4

Drying Conditions

| Active Agent Casting Solution Drying | | | | Backing Layer Drying | |
| --- | --- | --- | --- | --- | --- |
| Humidity (% RH) | Convection | Time (min) | 32° C. | CDA box @ RT (min) | 45° C. (min) |
| NA | NC | 0 | 30 | 30 | 90 |
| 75 | NC | 5 | 30 | 30 | 90 |
| 75 | NC | 15 | 30 | 30 | 90 |
| 85 | Low | 30 | 30 | 30 | 90 |
| 85 | High | 30 | 30 | 30 | 90 |
| NA | NC | 0 | 30 | 30 | 30 |
| 75 | NC | 15 | 30 | 30 | 30 |
| NA | NC | 0 | 30 | 30 | 90 |
| 75 | NC | 15 | 30 | 30 | 90 |
| NA | NC | 0 | 30 | 30 | 90 |
| 75 | NC | 15 | 30 | 30 | 90 |
| NA | NC | 0 | 30 | 0 | 120 |
| NA | NC | 0 | 30 | 30 | 120 |

Example 3

Microstructure Arrays with Backing Layer and Substrate

Microstructure arrays comprising an active agent and backing layer are prepared in accord with Examples 1 and 2. UV adhesive is dispensed on the backing layer formulation in the mold, covered with a 5 mL polycarbonate (PC) film to spread the adhesive and cured using a UV Fusion system. The UV curing dose is 1.6 J/cm$^2$. The molds are dried according to Table 5 which shows the drying conditions for the active agent formulation, backing layer and substrate. The molds are dried under vacuum at about 0.05 Torr at 35° C., at room temperature (RT), or a combination of 35° C. and RT.

TABLE 5

Substrate Drying Conditions

| Active Agent Casting Solution Drying | | | | Backing Layer | Final Drying | |
| --- | --- | --- | --- | --- | --- | --- |
| Humidity (% RH) | Convection | Time (min) | 32° C. (min) | Drying 45° C. (min) | RT (hrs) | 35° C. (hrs) |
| NA | NC | 0 | 30 | 90 | 0 | 0 |
| NA | NC | 0 | 30 | 90 | 0 | 16 |
| NA | NC | 0 | 30 | 90 | 0 | 16 |
| 85 | Low | 30 | 30 | 90 | 0 | 16 |
| 85 | High | 30 | 30 | 90 | 0 | 16 |
| 75 | NC | 15 | 30 | 30 | 16 | 0 |
| 75 | NC | 15 | 30 | 30 | 16 | 6 |
| 75 | NC | 15 | 30 | 90 | 16 | 0 |
| 75 | NC | 15 | 30 | 90 | 16 | 6 |
| 75 | NC | 15 | 30 | 90 | 0 | 16 |

RT—Room temperature

After drying, the microstructure array is demolded and die cut with an 11 or 16 mm punch.

Example 4

Microstructure Arrays

Microstructure arrays comprising an active agent are prepared using heating from under or below the microstructure mold. Liquid casting formulations comprising PTH as the API were prepared in accord with Example 1. A liquid casting formulation is prepared by dissolving at least 1.8 wt % PTH, 26 wt % Dextran 70, and 9 wt % Sorbitol in acetonitrile. An amount of liquid casting solution formulation is dispensed on a silicone mold and covered with a glass cover slip to spread the formulation on the mold. The mold is placed over a hot plate and circulating hot water in a chamber with high or low convection at 32° C. The mold is dried for 5, 10, or 20 minutes using low or high convection. The mold is then dried under vacuum at about 0.05 Torr at 35° C., at room temperature (RT), or a combination of 35° C. and RT. A control is dried in accord with Example 3 with an initial drying time of 30 minutes. The meniscus of the microstructures was measured with the results shown in FIG. 6. FIG. 9 shows a formulation dispensed in a mold and a meniscus after drying. The base height and meniscus height positions used for FIG. 6 are indicated.

Alternatively, a liquid casting formulation comprising an alternative protein (ProteinX) is prepared in accord with Example 1. A liquid casting formulation is prepared by dissolving at least 8 wt % ProteinX, 10 wt % Dextran 70, and 6 wt % Sorbitol in acetonitrile. An amount of liquid casting solution formulation is dispensed on a silicone mold and covered with a glass cover slip to spread the formulation on the mold. The mold is placed over a hot plate and circulating hot water in a chamber with high or low convection at 32° C. The mold is dried for 3, 5, or 10 minutes using low or high convection. The mold is then dried under vacuum at about 0.05 Torr at 35° C., at room temperature (RT), or a combination of 35° C. and RT.

An additional formulation is placed over a hot plate and circulating hot water in a chamber at high RH (about 10-95%) at 32° C. The mold is dried for 5 minutes using low convection. The mold is not dried under vacuum. A control was dried according to Example 3. The meniscus of the microstructures is measured with the results shown in FIG. 7.

Example 5

Microstructure Arrays with Reduced Solvent Content

Microstructure arrays comprising an active agent and backing layer are prepared including heating from under the mold. Liquid casting formulations are prepared by dissolving an API, polymer, sugar, Polysorbate 20 and EDTA in acetonitrile in accord with Example 1. An amount of liquid casting solution formulation is dispensed on a silicone mold and covered with a glass cover slip to spread the formulation on the mold. The mold is placed over a hot plate and circulating hot water in a chamber with high or low convection at 32° C. in accord with Example 4. A backing layer prepared in accord with Example 2 is dispensed on the mold. A thin film is cast by wiping the backing layer formulation. The mold is placed over a hot plate and circulating hot water in a chamber with high or low convection at 45° C. and ambient humidity. The % w/w residual solvent (ACN) is determined after 5, 10, 15, and 20 minutes with the results shown in FIG. 8.

Example 6

Dissolution of Arrays

Microstructure arrays (MSA) prepared either in accord with Examples 1-3 or without humidity controlled slow drying were observed under light microscope. The MSAs prepared in accord with Examples 1-3 were dried at 85% RH for 10 minutes. MSAs were immersed in an aqueous medium for about 10 minutes and the residual projections were observed under light microscope to estimate the geometry of the dried active agent and images were taken (FIGS. 3A-3C). FIG. 3A shows a microstructure array prepared using humidity controlled (85% RH) slow drying at room temperature for 10 minutes for the primary drying step after dissolution. FIGS. 3B and 3C show microstructure arrays prepared using a slow drying step without humidity control.

Example 7

Administration of a Microstructure Array

Microstructure arrays comprising an active agent are prepared in accord with Examples 1-3. Full-thickness pig skin is excised from the abdomen and then clipped and shaved to remove hair bristles. MSAs are applied to the shaved skin sites using an applicator or manually and are manually held in situ for a period of time (e.g. 5-15 minutes). Application sites are dye stained, tape stripped to remove background staining, and photographed to visualize the microstructure penetrations. Penetrations are quantified visually or by using an image analysis program. Skin penetration efficiency is calculated based on the theoretical number of microstructures expected for the MSA:

% SPE=100×(# penetrations/# microstructures)

After being photographed, the MSA are immersed in an aqueous extraction medium for about 30 minutes and the medium is analyzed by SEC-HPLC. The apparent delivered dose per unit and delivery efficiency are calculated with the formulas:

Apparent delivered dose=initial drug load−residual drug

% Drug delivery efficiency=100×Apparent delivered dose/initial drug load

Delivery efficiency for hPTH was about 85%.

Example 8

Microstructure Array Stability and Shelf Life

The in-process drug stability during fabrication of the MSAs is monitored by taking samples at key steps and analyzing the drug purity. For shelf life stability, the MSAs are stored at 5° C., 25° C. at 65% RH, and 40° C. at 75% RH. At predetermined time(s), the samples are taken and the drug purity is analyzed. Drug aggregation is measured by SEC-HPLC and chemical stability is measured by RP-HPLC. Deamidation of the drug is measured by IEX-HPLC. Where the active agent is a MAb (monoclonal antibody), the oxidation of methionine residues in the antibody is monitored by Lys-C proteolytic mapping using reverse phase HPLC.

MSAs comprising hPTH as the active agent were prepared in accord with Example 2, with or without methionine added as an antioxidant to the casting solution. MSAs were prepared using three different backing layer drying conditions with the results shown in Table 6.

TABLE 6

Effect of Backing Layer Drying on Purity of hPTH (1-34) in Arrays

| Active Agent | Backing Layer Drying | hPTH purity (area %) |
|---|---|---|
| hPTH (1-34) | 35° C. for 150 min | 99.8 ± 0.0 |
| hPTH (1-34) | 35° C. for 90 min, 45° C. for 30 min | 99.8 ± 0.3 |
| hPTH (1-34) | 45° C. for 90 min | 99.9 ± 0.0 |
| hPTH (1-34)* | 35° C. for 150 min | 99.7 ± 0.4 |
| hPTH (1-34)* | 35° C. for 90 min, 45° C. for 30 min | 99.9 ± 0.0 |
| hPTH (1-34)* | 45° C. for 90 min | 99.7 ± 0.4 |

*Casting solution contains methionine

Example 9

Casting Funnel Shaped Microstructure

A liquid drug solution prepared as described in Example 1 is dispensed onto a mold surface having funnel shaped cavities. The filled mold is pressurized to fill the cavities. The mold surface is wiped to remove excess liquid drug solution from the mold. After wiping, the mold with the drug solution is dried according to Table 2. During the drying, a solid dried matrix is formed in the distal microstructure cavities. This dried matrix fills a portion of the distal microstructures depending on the solid content in the liquid drug solution. To load higher doses of drug, the mold cavities are filled with liquid drug solution as much as possible to achieve the maximum dried solid matrix containing drug. A larger funnel volume results in greater solid matrix after drying, particularly in cylindrical shaped microstructures.

1. A method of making an array of microstructures comprising:
 (a) dissolving or suspending at least one therapeutic agent in a solvent to form a therapeutic agent solution or suspension;
 (b) dissolving at least one polymer in a solvent to form a polymer solution;
 (c) mixing the therapeutic agent solution or suspension and the polymer solution or suspension to form a polymer matrix solution or suspension;
 (d) dispensing the polymer matrix solution or suspension on a mold having an array of microstructure cavities;
 (e) filling the microstructure cavities in the mold;
 (f) removing excess solution or suspension polymer matrix on the mold surface;
 (g) drying the solution or suspension in a chamber having a partial pressure of water of about 0.01 mTorr to about 230 Torr at a temperature of about 5-50° C. or about 10-50° C.;
 (h) drying the solution or suspension at about 5-50° C. to form an array of microstructures; and
 (i) drying the microstructures under vacuum at about 5-50° C.

2. A method of making an array of microstructures comprising:
 (a') dissolving or suspending a therapeutic agent in water to form a therapeutic agent solution or suspension;
 (b') dissolving at least one polymer in water to form a polymer solution;
 (c') mixing the therapeutic agent solution or suspension and the polymer solution or suspension to form a polymer matrix solution or suspension;
 (d') dispensing the polymer matrix solution or suspension on a mold having an array of microstructure cavities;
 (e') filling the microstructure cavities in the mold;
 (f') removing excess solution or suspension on the mold surface;
 (g') drying the solution or suspension in a chamber having relative humidity of about 10-95% at a temperature of about 5-50° C.;
 (h') drying the solution or suspension at about 5-50° C. to form an array of microstructures; and
 (i') drying the microstructures under vacuum at about 5-50° C.

3. The method of embodiment 1 or 2, wherein the chamber uses convection, conduction, or radiation for drying.

4. The method of the combined or separate embodiments 1-3 further comprising:
 dispensing a basement or backing layer on the mold surface; and
 drying the basement or backing layer.

5. The method of embodiment 4, wherein drying the basement or backing layer comprises drying in an oven at about 5-50° C.

6. The method of the combined or separate embodiments 4 and 5, wherein drying the basement or backing layer comprises drying in a compressed dry air box with controlled air flow prior to drying in an oven.

7. The method of the combined or separate embodiments 1-6, further comprising:
 affixing the basement or backing layer to a substrate.

8. The method of embodiment 7, wherein the substrate is selected from a pressure sensitive adhesive and a UV cured adhesive.

9. The method of the combined or separate embodiments 7-8, further comprising: attaching the substrate adhesive to a metal, silicon, and/or polymer layer.

10. The method of the combined or separate embodiments 7-9, further comprising:
 using a nonwoven or porous film double coated with adhesive to affix the basement or backing layer to the substrate.

11. The method of the combined or separate embodiments 1-10, further comprising:
 demolding the microstructure tips or microstructure array.

12. The method of embodiment 10, wherein demolding comprises demolding after step (i) or (i').

13. The method of embodiment 10, wherein demolding comprises demolding after drying the basement or backing layer.

14. The method of the combined or separate embodiments 1-13, wherein prior to step (a) or (a'), the mold is subjected to a surface treatment over at least a portion of its surface prior to dispensing the polymer matrix solution or suspension which makes it easier for the solution or suspension to wet the mold surface.

15. The method of embodiment 14, wherein the surface treatment comprises coating at least a portion of the mold surface with a treatment selected from calcium carbonate, ethyl acetate, a silicone fluid, or oxygen plasma.

16. The method of the combined or separate embodiments 1-15, wherein prior to step (a) or (a'), the mold is subjected to a treatment which causes it to swell.

17. The method of the combined or separate embodiments 1-15, further comprising:
 applying a wetting agent to the mold prior to step (a) or (a').

18. The method of embodiment 17, wherein the wetting agent is a silicone polyether surfactant.

19. The method of the combined or separate embodiments 1-18, wherein step (e) or (e') comprises pressurization of at least about 10 psi above atmospheric.

20. The method of the combined or separate embodiments 1-18, wherein step (e) or (e') uses soluble gases.

21. The method of embodiment 20, wherein the soluble gas is selected from $CO_2$ and $CH_4$.

22. The method of the combined or separate embodiments 1-21, wherein one of steps (a) or (b) further comprises dissolving a sugar in the solvent.

23. The method of the combined or separate embodiments 1-22, wherein one of steps (a') or (b') further comprises dissolving a sugar in the solvent.

24. The method of the combined or separate embodiments 1-33, further comprising dissolving a sugar in the polymer matrix solution or suspension after step (c) or (c').

25. The method of the combined or separate embodiments 22-24, wherein the sugar is selected from sorbitol, sucrose, trehalose, fructose, or dextrose.

26. The method of the combined or separate embodiments 1-25, wherein one of steps (a) or (b) further comprises dissolving a surfactant in one of the solvents.

27. The method of the combined or separate embodiments 1-25, wherein one of steps (a') or (b') further comprises dissolving a surfactant in the solvent.

28. The method of the combined or separate embodiments 26-27, wherein the surfactant is selected from Polysorbate 20 or Polysorbate 80.

29. The method of the combined or separate embodiments 1-28, wherein one of steps (a) or (b) further comprises dissolving an antioxidant in one of the solvents.

30. The method of the combined or separate embodiments 1-29, wherein one of steps (a') or (b') further comprises dissolving an antioxidant in the solvent.

31. The method of the combined or separate embodiments 29-30, wherein the antioxidant is selected from methionine, cysteine, D-alpha tocopherol acetate, EDTA, or vitamin E.

32. The method of the combined or separate embodiments 1-31, wherein step (b) or (b') comprises dissolving about 10-40% by weight of the polymer in the solvent.

33. The method of the combined or separate embodiments 1-32, wherein the therapeutic agent is selected from a drug, a small molecule, a peptide or protein, or a vaccine.

34. The method of the combined or separate embodiments 1-33, wherein the suspension is a liquid in liquid suspension.

35. The method of the combined or separate embodiments 1-33, wherein the suspension is a solid in liquid suspension.

36. A method of making an array of microstructures comprising:
(a) dissolving or suspending at least one therapeutic agent in a solvent to form a therapeutic agent solution or suspension;
(b) dissolving at least one polymer in a solvent to form a polymer solution;
(c) mixing the therapeutic agent solution or suspension and the polymer solution or suspension to form a polymer matrix solution or suspension;
(d) dispensing the polymer matrix solution or suspension on a mold having an array of microstructure cavities;
(e) filling the microstructure cavities in the mold;
(f) removing excess solution or suspension polymer matrix on the mold surface;
(g) drying the solution or suspension in a chamber from below at a temperature of about 5-50° C. or about 10-50° C.; and
(i) drying the microstructures under vacuum at about 5-50° C.

37. The method of embodiment 35, wherein the mold surface is heated from below using conduction or radiation to maintain a temperature of about 5-50° C. for the polymer matrix solution or suspension.

38. The method of the combined or separate embodiments 36-37, further comprising:
dispensing a basement or backing layer on the mold surface; and
drying the basement or backing layer from below.

39. The method of the combined or separate embodiments 36-38, wherein drying the basement of backing layer comprises drying on the mold from below using conductive or radiative heating.

40. The method of the combined or separate embodiments 6-39.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A method of making an array of microstructures comprising:
    (a) dissolving or suspending at least one therapeutic agent and at least one polymer in one or more solvents to form a polymer matrix solution or suspension;
    (b) dispensing the polymer matrix solution or suspension on a mold having an array of microstructure cavities;
    (c) filling the microstructure cavities in the mold with the polymer matrix solution or suspension;
    (d) removing excess polymer matrix solution or suspension on the mold surface;
    (e) a first drying step comprising drying the polymer matrix solution or suspension at a temperature of about 5-50° C. in a chamber having a partial pressure of water of about 0.01 mTorr to about 203 Torr or a relative humidity of about 50-95% for about 5-30 minutes;
    (f) a second drying step comprising drying the polymer matrix solution or suspension at about 5-50° C. for about 30 minutes in an oven without controlled partial pressure of water or relative humidity to form an array of microstructures; and
    (g) drying the microstructures under vacuum at about 5-50° C.

2. The method of claim 1, wherein step (a) comprises:
    (i) dissolving or suspending the at least one therapeutic agent in a first solvent to form a therapeutic agent solution or suspension;
    (ii) dissolving the at least one polymer in a second solvent to form a polymer solution or suspension; and
    (iii) mixing the therapeutic agent solution or suspension and the polymer solution or suspension to form the polymer matrix solution or suspension.

3. The method of claim 1, wherein the chamber uses convection, conduction, or radiation for drying.

4. The method of any previous claim, further comprising:
dispensing a basement or backing layer on the mold surface; and
drying the basement or backing layer.

5. The method of claim 4, wherein drying the basement or backing layer comprises drying in an oven at about 5-50° C.

6. The method of claim 4, wherein drying the basement or backing layer comprises drying in a compressed dry air box with controlled air flow prior to drying in an oven.

7. The method of any one of claim 4, further comprising:
affixing the basement or backing layer to a substrate.

8. The method of claim 7, wherein the substrate is selected from a pressure sensitive adhesive and a UV cured adhesive.

9. The method of claim 7, further comprising:
affixing the basement or backing layer to the substrate using a nonwoven or porous film double coated with adhesive.

10. The method of claim 1, further comprising:
demolding the microstructure array.

11. The method of claim 4, further comprising demolding the microstructure array after drying the basement or backing layer.

12. The method of claim 1, further comprising:
applying a wetting agent to the mold prior to step (b).

13. The method of claim 12, wherein the wetting agent is selected from calcium carbonate, ethyl acetate, a silicone fluid, oxygen plasma, or a silicone polyether surfactant.

14. The method of claim 1, wherein step (c) comprises pressurization of at least about 10 psi above atmospheric.

15. The method of claim 1, wherein step (c) uses soluble gases.

16. The method of claim 15, wherein the soluble gas is selected from $CO_2$ and $CH_4$.

17. The method of claim 1, wherein step (a) further comprises dissolving at least one of a sugar, a surfactant, or an antioxidant in the one or more solvents.

18. The method of claim 1, further comprising dissolving a sugar in the polymer matrix solution or suspension after step (a).

19. The method of claim 17, wherein the sugar is selected from sorbitol, sucrose, trehalose, fructose, or dextrose.

20. The method of claim 17, wherein the surfactant is selected from Polysorbate 20 or Polysorbate 80.

21. The method of claim 17, wherein the antioxidant is selected from methionine, cysteine, D-alpha tocopherol acetate, EDTA, or vitamin E.

22. The method of claim 1, wherein step (a) comprises dissolving about 10-40% by weight of the at least one polymer in the one or more solvents.

23. The method of claim 1, wherein the at least one therapeutic agent is selected from a drug, a small molecule, a peptide or protein, or a vaccine.

24. The method of claim 1, wherein the suspension is a liquid in liquid suspension or a solid in liquid suspension.

25. The method of claim 2, wherein at least one of the first or second solvents is water.

* * * * *